(12) United States Patent
Bahuguna et al.

(10) Patent No.: US 11,765,549 B2
(45) Date of Patent: *Sep. 19, 2023

(54) CONTACT TRACING INVOLVING AN INDEX CASE, BASED ON COMPARING GEO-TEMPORAL PATTERNS THAT INCLUDE MOBILITY PROFILES

(71) Applicant: Polaris Wireless, Inc., Mountain View, CA (US)

(72) Inventors: Anjul Bahuguna, San Ramon, CA (US); Scot Douglas Gordon, Redmond, WA (US); Robert Lewis Martin, Antioch, CA (US)

(73) Assignee: Polaris Wireless, Inc., Mountain View, CA (US)

( * ) Notice: Subject to any disclaimer, the term of this patent is extended or adjusted under 35 U.S.C. 154(b) by 307 days.

This patent is subject to a terminal disclaimer.

(21) Appl. No.: 17/214,842

(22) Filed: Mar. 27, 2021

(65) Prior Publication Data
US 2021/0321220 A1 Oct. 14, 2021

Related U.S. Application Data

(60) Provisional application No. 63/007,674, filed on Apr. 9, 2020, provisional application No. 63/007,492, filed
(Continued)

(51) Int. Cl.
*H04W 4/00* (2018.01)
*H04W 4/029* (2018.01)
(Continued)

(52) U.S. Cl.
CPC ............ *H04W 4/029* (2018.02); *G16H 50/30* (2018.01); *G16H 50/80* (2018.01); *G16H 70/60* (2018.01);
(Continued)

(58) Field of Classification Search
CPC ..... H04W 4/029; H04W 4/023; H04W 4/025; H04W 8/14; G16H 50/30; G16H 50/80; G16H 70/60; G16H 10/60; G16H 40/67
(Continued)

(56) References Cited

U.S. PATENT DOCUMENTS

2016/0306934 A1\* 10/2016 Sperry .................... G06F 3/147
2017/0024531 A1\* 1/2017 Malaviya ............... G16H 50/30
(Continued)

OTHER PUBLICATIONS

Notice of Allowance, USPTO, U.S. Appl. No. 17/214,840, dated Aug. 24, 2022.

*Primary Examiner* — Tanmay K Shah
(74) *Attorney, Agent, or Firm* — McGeary Cukor, LLC; Kenneth Ottesen; Jason Paul DeMont

(57) ABSTRACT

A method for performing contact tracing. An analysis system performing the method receives geo-temporal data comprising location data points for various wireless terminals, including the wireless terminals being used by people diagnosed as having a specified disease and the wireless terminals of others, one of whom having possibly infected those diagnosed with the disease. Based on filtering the geo-temporal data, the analysis system generates relatively-condensed mobility profiles that are representative of each person's locations and movements, and analyzes the mobility profiles. Through careful selections of various parameters based on the disease that is being analyzed, the mobility profiles are used instead of the relatively large amounts of geo-temporal data, to represent users of wireless terminals and to determine their interactions in regard to disease transmission.

20 Claims, 11 Drawing Sheets

Related U.S. Application Data on Apr. 9, 2020, provisional application No. 63/007,679, filed on Apr. 9, 2020.

(51) Int. Cl.
| | | |
|---|---|---|
| *G16H 50/80* | (2018.01) | |
| *G16H 50/30* | (2018.01) | |
| *G16H 70/60* | (2018.01) | |
| *H04W 4/02* | (2018.01) | |
| *H04W 8/14* | (2009.01) | |

(52) U.S. Cl.
CPC .......... *H04W 4/023* (2013.01); *H04W 4/025* (2013.01); *H04W 8/14* (2013.01)

(58) Field of Classification Search
USPC ...................................... 455/456.3
See application file for complete search history.

(56) References Cited

U.S. PATENT DOCUMENTS

| | | | |
|---|---|---|---|
| 2018/0052970 A1* | 2/2018 | Boss | ............... G06F 21/35 |
| 2020/0322868 A1 | 10/2020 | Claffey et al. | |
| 2020/0406860 A1 | 12/2020 | Mai et al. | |

* cited by examiner

| | SUN | MON | TUE | WED | THU | FRI | SAT |
|---|---|---|---|---|---|---|---|
| AM 7:00 | | ZONE 1 | ZONE 1 | ZONE 1 | ZONE 1 | ZONE 1 | |
| 7:30 | | | | | | | |
| 8:00 | | ZONE 3 | ZONE 3 | ZONE 3 | ZONE 3 | ZONE 3 | |
| 8:30 | | ZONE 4 | ZONE 4 | ZONE 4 | ZONE 4 | ZONE 4 | |
| 9:00 | | ZONE 5 | ZONE 5 | ZONE 5 | ZONE 5 | ZONE 5 | |
| 9:30 | | | ZONE 4 | | | | |
| 10:00 | | | ZONE 5 | | | | |
| 10:30 | ZONE 1 | ZONE 2 | ZONE 2 | ZONE 2 | ZONE 2 | ZONE 2 | ZONE 1 |
| 11:00 | | | | | | | |
| 11:30 | | | ZONE 5 | | | | |
| PM 12:00 | | | ZONE 2 | | | | |
| 12:30 | | | | | | | |
| 1:00 | | ZONE 5 | ZONE 5 | | | | |
| 1:30 | | ZONE 4 | ZONE 4 | | | | |
| 2:00 | | ZONE 3 | ZONE 3 | | | | |
| 2:30 | | | | | | | |
| 3:00 | | | | ZONE 5 | ZONE 5 | ZONE 5 | |
| 3:30 | | | | ZONE 4 | ZONE 4 | ZONE 4 | |
| 4:00 | | | | ZONE 3 | ZONE 3 | ZONE 3 | |
| 4:30 | | | | | | | |
| 5:00 | | ZONE 1 | ZONE 1 | ZONE 1 | ZONE 1 | ZONE 1 | |
| 5:30 | | | | | | | |
| 6:00 | | | | | | | |
| 6:30 | | | | | | | |

| | SUN | MON | TUE | WED | THU | FRI | SAT |
|---|---|---|---|---|---|---|---|
| AM 7:00 | | ZONE 6 | ZONE 6 | ZONE 6 | ZONE 6 | ZONE 6 | |
| 7:30 | | | | | | | |
| 8:00 | | ZONE 3 | | ZONE 3 | ZONE 3 | ZONE 3 | |
| 8:30 | | ZONE 4 | ZONE 4 | ZONE 4 | ZONE 4 | ZONE 4 | |
| 9:00 | | ZONE 8 | ZONE 8 | ZONE 8 | ZONE 8 | ZONE 8 | |
| 9:30 | | | | | | | |
| 10:00 | | | | | | | |
| 10:30 | ZONE 6 | ZONE 7 | ZONE 7 | ZONE 7 | ZONE 7 | ZONE 7 | ZONE 6 |
| 11:00 | | | | | | | |
| 11:30 | | | | | | | |
| PM 12:00 | | | | | | | |
| 12:30 | | | | | | | |
| 1:00 | | | | | | | |
| 1:30 | | | | | | ZONE 7 | |
| 2:00 | | ZONE 8 | ZONE 8 | ZONE 8 | ZONE 8 | ZONE 8 | |
| 2:30 | | ZONE 4 | ZONE 4 | ZONE 4 | ZONE 4 | ZONE 4 | |
| 3:00 | | ZONE 3 | ZONE 3 | ZONE 3 | ZONE 3 | ZONE 3 | |
| 3:30 | | ZONE 6 | ZONE 6 | ZONE 6 | ZONE 6 | ZONE 6 | |
| 4:00 | | | | | | | |
| 4:30 | | | | | | | |
| 5:00 | | | | | | | |
| 5:30 | | | | | | | |
| 6:00 | | | | | | | |
| 6:30 | | | | | | | |

Figure 7B — 702, 706, 708, 710

| | SUN | MON | TUE | WED | THU | FRI | SAT |
|---|---|---|---|---|---|---|---|
| AM 7:00 | | ZONE 9 | ZONE 9 | ZONE 9 | ZONE 9 | ZONE 9 | |
| 7:30 | | ZONE 10 | ZONE 10 | ZONE 10 | ZONE 10 | ZONE 10 | |
| 8:00 | | ZONE 11 | ZONE 11 | ZONE 11 | ZONE 11 | ZONE 11 | |
| 8:30 | | | | | | | |
| 9:00 | ZONE 9 | | | | | | ZONE 9 |
| 9:30 | | | | | | | |
| 10:00 | | | | | | | |
| 10:30 | | | ZONE 2 | ZONE 2 | ZONE 2 | ZONE 2 | |
| 11:00 | | ZONE 2 | | | | | |
| 11:30 | | | | | | | |
| PM 12:00 | | | | | | | |
| 12:30 | | | | | | | |
| 1:00 | | | | | | | |
| 1:30 | | | | | | | |
| 2:00 | | | | | | | |
| 2:30 | | | | | | | |
| 3:00 | | | | | | | |
| 3:30 | | | ZONE 11 | | | | |
| 4:00 | | ZONE 11 | ZONE 10 | ZONE 11 | ZONE 11 | ZONE 11 | |
| 4:30 | | ZONE 10 | | ZONE 10 | ZONE 10 | ZONE 10 | |
| 5:00 | | | ZONE 9 | | | | |
| 5:30 | | ZONE 9 | | ZONE 9 | ZONE 9 | ZONE 9 | |
| 6:00 | | | | | | | |
| 6:30 | | | | | | | |

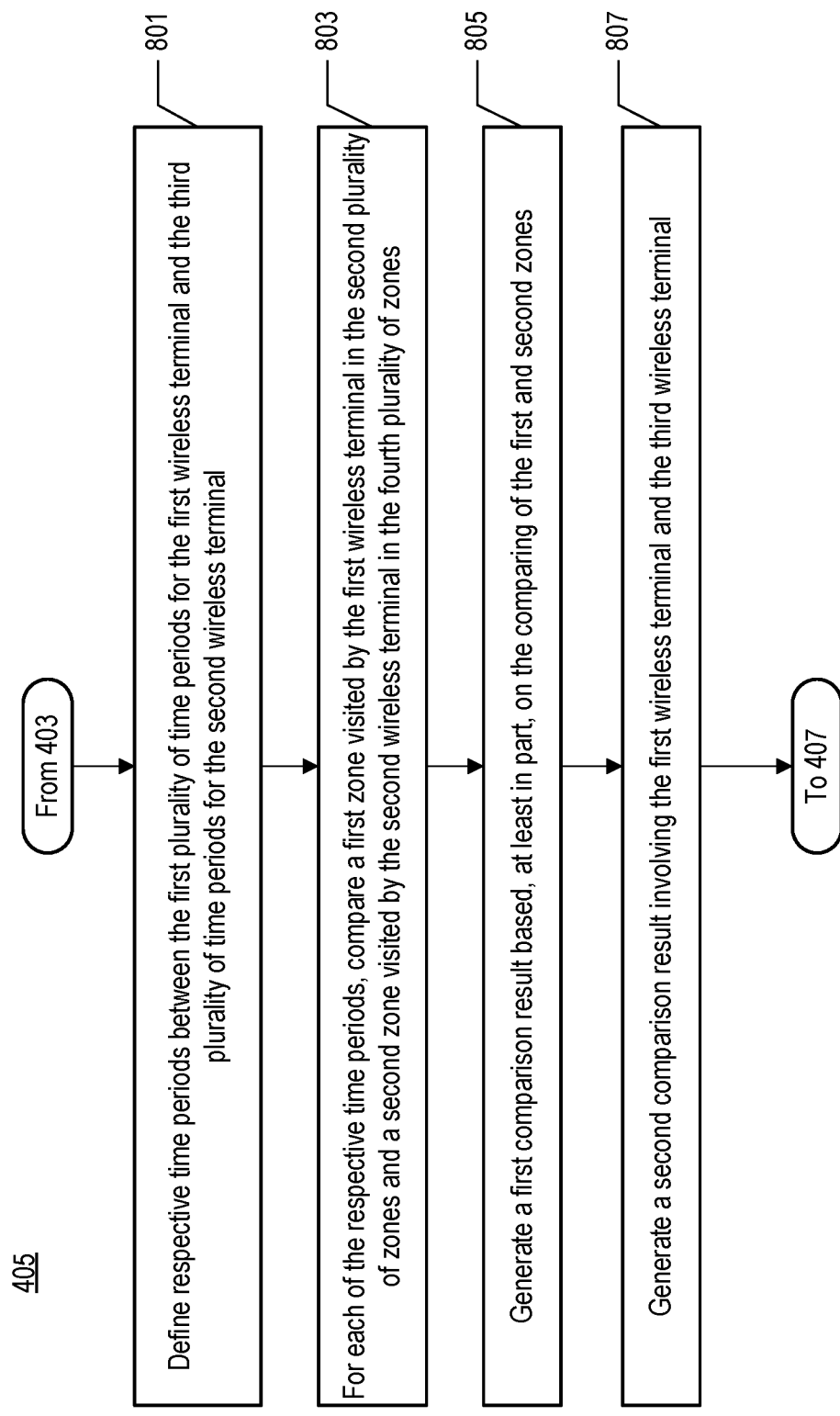

CONTACT TRACING INVOLVING AN INDEX CASE, BASED ON COMPARING GEO-TEMPORAL PATTERNS THAT INCLUDE MOBILITY PROFILES

CROSS REFERENCE TO RELATED APPLICATIONS

This application claims the benefit of:
(i) U.S. Provisional Application Ser. No. 63/007,492, filed Apr. 9, 2020, and
(ii) U.S. Provisional Application Ser. No. 63/007,674, filed Apr. 9, 2020, and
(iii) U.S. Provisional Application Ser. No. 63/007,679, filed Apr. 9, 2020,
all of which are incorporated by reference. If there are any contradictions or inconsistencies in language between this application and any document that has been incorporated by reference that might affect the interpretation of the claims in this application, the claims in this application should be interpreted to be consistent with the language in this application.

This application is related to "Contact Tracing Based On Comparing Geo-Temporal Patterns Of Wireless Terminals, Including Mobility Profiles," U.S. application Ser. No. 17/214,840, filed on Mar. 27, 2021 and incorporated by reference herein.

FIELD OF THE INVENTION

The present invention relates to medicine in general, and, more particularly, to the control of infectious diseases.

BACKGROUND OF THE INVENTION

There are some diseases that a person can develop because of the presence or absence of specific sequences in the person's genome. Also, there are some diseases that a person can develop because of environmental factors in the person's presence.

In contrast, there are some diseases that a person can develop only when they come into contact, directly or indirectly, with a person who already has the disease. These infectious diseases include measles, smallpox, and coronavirus disease 2019, or "COVID-19." The path to preventing infectious diseases includes:
  i. the elimination of the source of the pathogen causing the disease, and
  ii. the development of vaccines, and
  iii. the development of herd immunity, and
  iv. social distancing, and
  v. identifying and quarantining those people who are infected to prevent them from infecting others, and
  vi. identifying and isolating those people who have come into contact—directly or indirectly—with a person who is already infected so as to prevent the further spread of the disease.

The process of identifying those people who have, or might have, come into contact, directly or indirectly, with an infected entity is called "contact tracing." Because the modern world comprises inexpensive and widely-used modes of local- and long-distance transportation, and because people regularly come into proximity with many people, the process of contact tracing is very difficult.

Some contact tracing methods involve the use of software applications, or "apps," executing on wireless terminals such as smartphones, which operate within a telecommunications network. FIG. 1 depicts a diagram of the salient components of telecommunications system 100, in the prior art. Telecommunications system 100 comprises: wireless terminals 101, 102, and 103, cellular base stations 104-1, 104-2, and 104-3, Wi-Fi base stations 105-1 and 105-2, wireless switching system 111, and location system 112. Telecommunications system 100 provides wireless telecommunications service to all wireless terminals within its coverage area.

Data that is generated by system 100 can suggest to an investigator (e.g., an epidemiologist, etc.) which:
  i. persons or persons might have had contact with an infected or infectious person, or
  ii. animals (e.g., cats, ferrets, bats, etc.) that might have had contact with an infected or infectious person, or
  iii. stationary objects (e.g., door knobs, countertop, etc.) might have been in the vicinity of an infected or infectious person, or
  iv. mobile objects (e.g., cars, trucks, trains, airplanes, bicycles, etc.) might have conveyed an infected or infectious person, or
  v. geographic locations where an infected or infection person might have been, or
  vi. any combination of i, ii, iii, iv, and v.

For example, an infected entity's geo-location history can be retrieved from location system 112 and, once a contact is identified, the contact's geo-location history can also be retrieved.

Contacts can be identified conventionally by asking about the infected entity's activities and the activities and roles of the people around them since onset of illness. Contacts can be anyone who has been in contact with an infected entity: family members, work colleagues, friends, health care providers, and others. All persons considered to have contact with the infected entity should be listed as contacts. However, relying on knowing the infected entity's activities and the activities and roles of the people around them since onset of illness is flawed. This is because it often relies on the infected entity's recollection, which is imperfect or incomplete.

Digital contact tracing apps that execute on a smartphone attempt to identify possible exposures to an infected entity. When the app is enabled to provide exposure notifications, the phone begins using Bluetooth (or another short-range communications protocol) to scan constantly for nearby phones that are using the same app and doing the same thing. When two phones connect with each other, they exchange identity codes, which are typically anonymous for privacy reasons. A phone records how long its user spends around the other phone and estimates how far away the other phone is. It does so based on a number of factors such as the strength of signals received from the other phone. If the user tests positive for a disease, other people who have been exposed to the infected entity can be notified, based on the identity codes exchanged.

In some ways, using a contact tracing app to track the infected entity's contact with other people who are also using the same app can be an improvement over relying merely on the infected entity's recollection. However, there are still disadvantages in relying on such an app. A key disadvantage is requiring a sufficient number of people within a population to be using an app that, at a minimum, must be able to detect an exposure and notify either its user or the appropriate health authority.

SUMMARY OF THE INVENTION

The present invention enables the control of infectious diseases, without at least some of the disadvantages in the prior art. A network-centric, geo-temporal analysis system disclosed herein receives geo-temporal data comprising location data points for various wireless terminals, including the wireless terminals being used by people diagnosed as having a specified disease and the wireless terminals of others, one of whom possibly having infected those diagnosed with the disease. Based on filtering the geo-temporal data, the analysis system generates mobility profiles that are representative of each person's locations and movements, including a first mobility profile for a first wireless terminal, a second mobility profile for a second wireless terminal, and a third mobility profile for a third wireless terminal. For example, the first wireless terminal can be that of a candidate index case, and the second and third wireless terminals can be those of people who are infected with the disease. In some scenarios regarding the users of the second and third terminals, they have definitely, or at least probably, not transmitted the disease to each other, as they have not crossed or abutted each other's path within a given timeframe, as reflected in their geo-temporal data.

A "mobility profile" can be regarded as a correlation of geographic zones to time periods for a wireless terminal. Each of the geographic zones is an aggregation of location data points, in which there are more location data points than there are zones and each data point is capable of representing an infinite number of possible geolocations, in terms of latitude, longitude, and/or elevation. Accordingly, generating the first mobility profile comprises defining a first profile time interval that comprises a first plurality of time periods, followed by aggregating, over the first profile time interval, selections of the location data for the first wireless terminal into corresponding zones in a second plurality of zones.

The first profile time interval, the time periods, and the zones are definable by one or more attributes, wherein the one or more attributes are based on characteristics of a disease that the second user is diagnosed as having. Such characteristics include (i) when an infected person is contagious, (ii) the mode(s) of transmission, (iii) the surface lifespan or stability of a pathogen, and (iv) the persistence of the pathogen, for example and without limitation.

The geo-temporal analysis system generates the second mobility profile in a similar way, by defining a second profile time interval that comprises a third plurality of time periods, then by aggregating, over the second profile time interval, selections of the location data for the second wireless terminal into corresponding zones in a fourth plurality of zones. The analysis system then compares the first mobility profile and the second mobility profile, resulting in a first comparison result. The analysis system generates an indication of contact based on the first comparison result exceeding a threshold that indicates a relative likelihood that the first and second user have come into contact with each other.

Similarly, the geo-temporal analysis system generates the third mobility profile for the user of the third wireless terminal and compares the first mobility profile and the third mobility profile, resulting in a second comparison result. The analysis system can generate an indication of contact based on the second comparison result exceeding a threshold that indicates a relative likelihood that the first and third user have come into contact with each other. Additionally, the analysis system can generate an indication of contact based on the combined results of multiple comparisons of mobility profiles, adding further evidence that the first user is the index case in regard to having exposed the second and third user to the pathogen causing the disease.

Contact tracing through the use of mobility profiles can provide a faster way of determining whether a first user of a first wireless terminal has infected a second user of a second wireless terminal and a third user of a third wireless terminal, who have been diagnosed with a particular disease. The geo-temporal analysis system of the illustrative embodiment generates and compares the relatively-condensed mobility profiles, through careful selections of profile time interval, time periods within each profile time interval, and geographic zones that correlate to the time periods, wherein the selections are based on the disease that is being analyzed. Advantageously, the mobility profiles are compared instead of the relatively large amounts of geo-temporal data in order to represent the users of the wireless terminals and to determine their interactions in regard to disease transmission. Moreover, the mobility profiles can be used for contact tracing even in the absence of any digital contact tracing app being available.

A first method for determining whether a first user of a first wireless terminal is an index case of a first disease, comprises: receiving location data for the first wireless terminal; generating a first mobility profile for the first wireless terminal, a second mobility profile for a second wireless terminal used by a second user, and a third mobility profile for a third wireless terminal used by a third user, wherein the generating of the first mobility profile comprises: (i) defining a first profile time interval that comprises a first plurality of time periods, the first profile time interval being defined by a first attribute, wherein the first attribute is based on a first disease that both the second user and the third user are diagnosed as having, (ii) aggregating, over the first profile time interval, selections of the location data for the first wireless terminal into corresponding zones in a second plurality of zones, and (iii) relating the zones in the second plurality to corresponding time periods in the first plurality; comparing the first mobility profile and the second mobility profile, resulting in a first comparison result; comparing the first mobility profile and the third mobility profile, resulting in a second comparison result; and generating an indication of contact based at least one of (i) the first comparison result and (ii) the second comparison result exceeding a first threshold that indicates a relative likelihood that the first user has come into contact with at least one of (i) the second user and (ii) the third user, respectively.

A second method for determining whether a first user of a first wireless terminal is an index case of a first disease, comprises: receiving location data for the first wireless terminal; generating a first mobility profile for the first wireless terminal, a second mobility profile for a second wireless terminal used by a second user, and a third mobility profile for a third wireless terminal used by a third user, wherein the generating of the first mobility profile comprises: (i) defining a first profile time interval that comprises a first plurality of time periods, the first profile time interval being defined by a first point in time and a second point in time, wherein the first point in time is based on when symptoms of a first disease appear for the second user, and wherein the second point in time is based on when symptoms of a first disease appear for the third user, (ii) aggregating, over the first profile time interval, selections of the location data for the first wireless terminal into corresponding zones in a second plurality of zones, and (iii) relating the zones in the second plurality to corresponding time periods in the first plurality; comparing the first mobility profile and the second mobility profile, resulting in a first comparison result; comparing the first mobility profile and the third mobility profile, resulting in a second comparison result; and generating an indication of contact based on a first combination of (i) the first comparison result and (ii) the second comparison result exceeding a threshold that indicates a relative likelihood that the first user has come into contact with both (i) the second user and (ii) the third user.

A third method for determining whether a first user of a first wireless terminal is an index case of a first disease, comprises: receiving location data for the first wireless terminal; generating a first mobility profile for the first wireless terminal, a second mobility profile for a second wireless terminal used by a second user, and a third mobility profile for a third wireless terminal used by a third user, wherein the generating of the first mobility profile comprises: (i) defining a first profile time interval that comprises a first plurality of time periods, the first profile time interval being defined by a first point in time and a second point in time, wherein the first point in time is based on when symptoms of a first disease appear for the second user, wherein the second point in time is based on when symptoms of a first disease appear for the third user, and wherein the length of at least one of the time periods in the first plurality of time periods is based on a mode of transmission of the first disease, (ii) aggregating, over the first profile time interval, selections of the location data for the first wireless terminal into corresponding zones in a second plurality of zones, and (iii) relating the zones in the second plurality to corresponding time periods in the first plurality; comparing the first mobility profile and the second mobility profile, resulting in a first comparison result; comparing the first mobility profile and the third mobility profile, resulting in a second comparison result; and generating an indication of contact based at least one of (i) the first comparison result and (ii) the second comparison result exceeding a first threshold that indicates a relative likelihood that the first user has come into contact with at least one of (i) the second user and (ii) the third user, respectively.

BRIEF DESCRIPTION OF THE DRAWINGS

FIGS. 7A, 7B, and 7C depict mobility profiles 701, 702, and 703, respectively.

FIG. 8 depicts a flowchart of the salient sub-operations of operation 405.

DEFINITIONS

Figure 1:
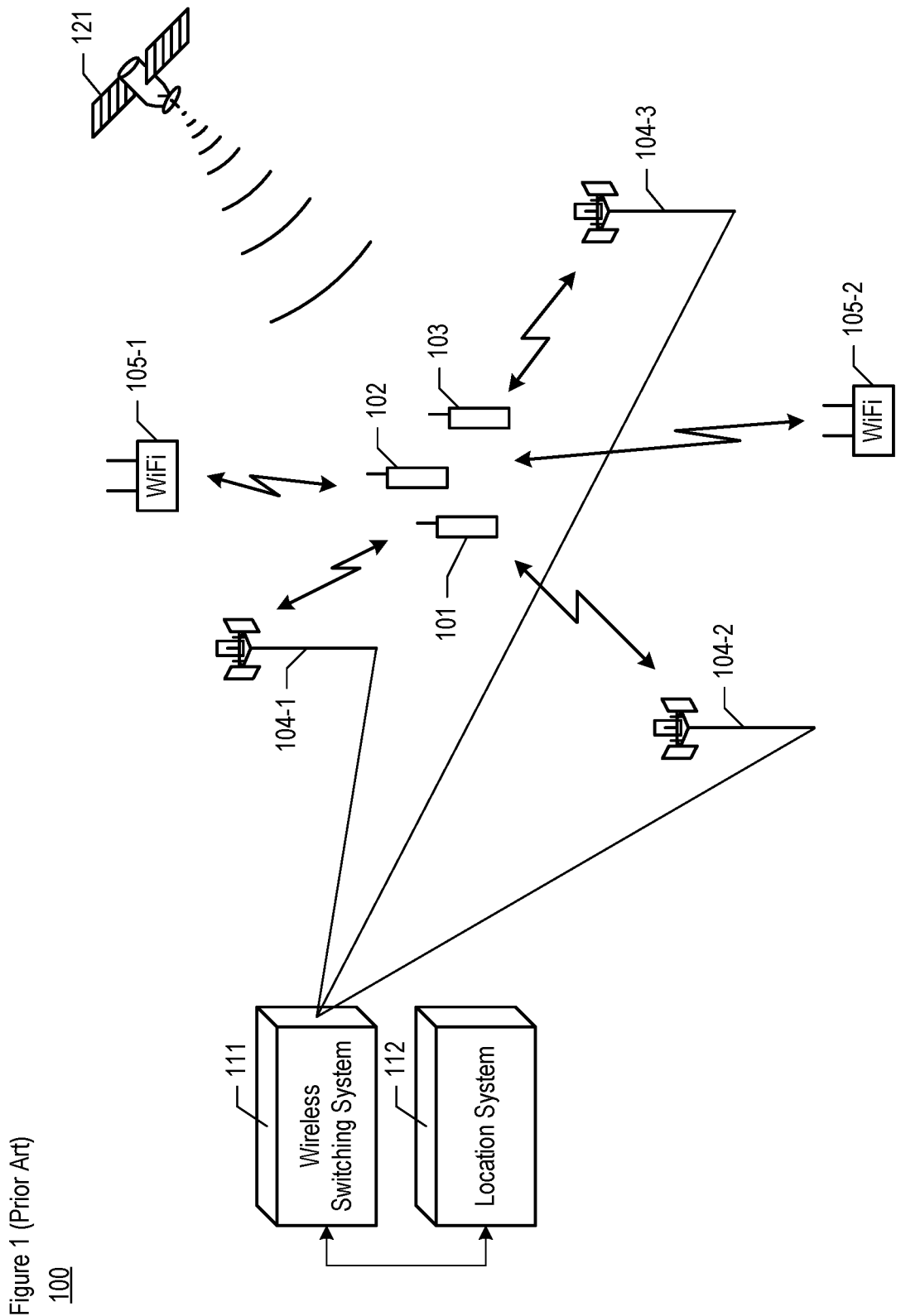
FIG. 1 depicts a diagram of the salient components of telecommunications system 100, in the prior art.

Based on—For the purposes of this specification, the term "based on" is defined as "being dependent on" in contrast to "being independent of". The value of Y is dependent on the value of X when the value of Y is different for two or more values of X. The value of Y is independent of the value of X when the value of Y is the same for all values of X. Being "based on" includes both functions and relations.

Contact—For the purposes of this specification, the term "contact" and its inflected forms is defined as a person, animal, stationary object, mobile object, or geographic location that might have acquired a pathogen from an infected entity.

Contact Tracing—For the purposes of this specification, the term "contact tracing" is defined as the process of identifying the contacts who might have come into contact with an infected entity and subsequent collection of further information about these contacts.

Generate—For the purposes of this specification, the infinitive "to generate" and its inflected forms (e.g., "generating", "generation", etc.) should be given the ordinary and customary meaning that the terms would have to a person of ordinary skill in the art at the time of the invention.

Geo-Temporal Attribute—For the purposes of this specification, the term "geo-temporal attribute" is defined as a characteristic that is associated, or can be associated, with a wireless terminal and comprises (i) a datum that indicates a location, and (ii) a temporal datum that corresponds to the location, e.g., timestamp, a point in time, a period of time, a duration, etc. A geo-temporal attribute can be based on one or more records of geo-temporal data. Examples of geo-temporal attributes are provided elsewhere herein.

Geo-Temporal Data—For the purposes of this specification, the term "geo-temporal data," or "spatiotemporal data" within a geographic context, is defined as data that comprises (i) a datum that indicates a location (e.g., of a wireless terminal, etc.), and (ii) a temporal datum that corresponds to the location, e.g., a timestamp, a point in time, a period of time, a duration, etc. Data that indicates locations is "location data."

Geo-Temporal Pattern—For the purposes of this specification, the term "geo-temporal pattern" is a representation of movement of a wireless terminal—and, by association, the wireless terminal's user or subscriber—among one or more locations as a function of time. It is defined by a composite of attributes of a wireless terminal, including at least one geo-temporal attribute. A geo-temporal pattern might also be defined by other attributes, such as the type of wireless terminal, or certain kinds of calls associated with the wireless terminal at certain locations and/or times, or the data (if any) transmitted between the wireless terminal and a different wireless terminal at certain locations and/or times. A geo-temporal pattern typically reflects attribute data that was gathered over an extended period of time, e.g., minutes, hours, days, weeks, months, etc. but is not so limited. Examples of a geo-temporal pattern are provided elsewhere herein and include, but are not limited to, a subscriber mobility profile, a subscriber behavior model, one or more clusters, one or more records of geo-temporal data.

Incubation Period—For the purposes of this specification, the term "incubation period" is defined as the period between exposure to an infection and the appearance of the first symptoms.

Infected Entity—For the purposes of this specification, the term "infected entity" is defined as the process of identification of a person who is infected, or is suspected of being infected, with a predetermined disease or diseases. An infected entity is sometimes referred to as the "index case," in the context of the index (as the "infecting person") first bringing a disease into a group of people.

Location—For the purposes of this specification, the term "location" is defined as a zero-dimensional point, a finite one-dimensional path segment, a finite two-dimensional surface area, or a finite three-dimensional volume. Thus, a location can be described, for example, by a street address, geographic coordinates, a perimeter, a geofence, a cell ID, or an enhanced cell ID.

Mobility Profile—For the purposes of this specification, the term "mobility profile" is defined as a correlation of geographic zones to time periods for a wireless terminal, wherein the geographic zones are aggregations of locations.

Mode of Transmission—For the purposes of this specification, the term "mode of transmission" is defined as the means by which a pathogen causing communicable disease is passed from an infected host or group to a particular individual or group.

Processor—For the purposes of this specification, a "processor" is defined as hardware or hardware and software that performs mathematical and/or logical operations.

Radio—For the purposes of this specification, a "radio" is defined as hardware or hardware and software that is capable of telecommunications via an unguided (i.e., wireless) radio signal of frequency less than 600 GHz.

Receive—For the purposes of this specification, the infinitive "to receive" and its inflected forms (e.g., "receiving", "received", etc.) should be given the ordinary and customary meaning that the terms would have to a person of ordinary skill in the art at the time of the invention.

Transmit—For the purposes of this specification, the infinitive "to transmit" and its inflected forms (e.g., "transmitting", "transmitted", etc.) should be given the ordinary and customary meaning that the terms would have to a person of ordinary skill in the art at the time of the invention.

Wireless Terminal—For the purposes of this specification, the term "wireless terminal" is defined as a device that is capable of telecommunications without a wire or tangible medium. A wireless terminal can be mobile or immobile. A wireless terminal can transmit or receive or transmit and receive. A wireless terminal is also commonly called a smartphone, a cellular telephone ("cellphone"), a wireless transmit/receive unit (WTRU), a user equipment (UE), a mobile station, wireless handset, a fixed or mobile subscriber unit, a pager, a personal digital assistant (PDA), an Internet of Things (IoT) device, a computer, or any other type of device capable of operating in a wireless environment are examples of wireless terminals.

DETAILED DESCRIPTION

Figure 2:
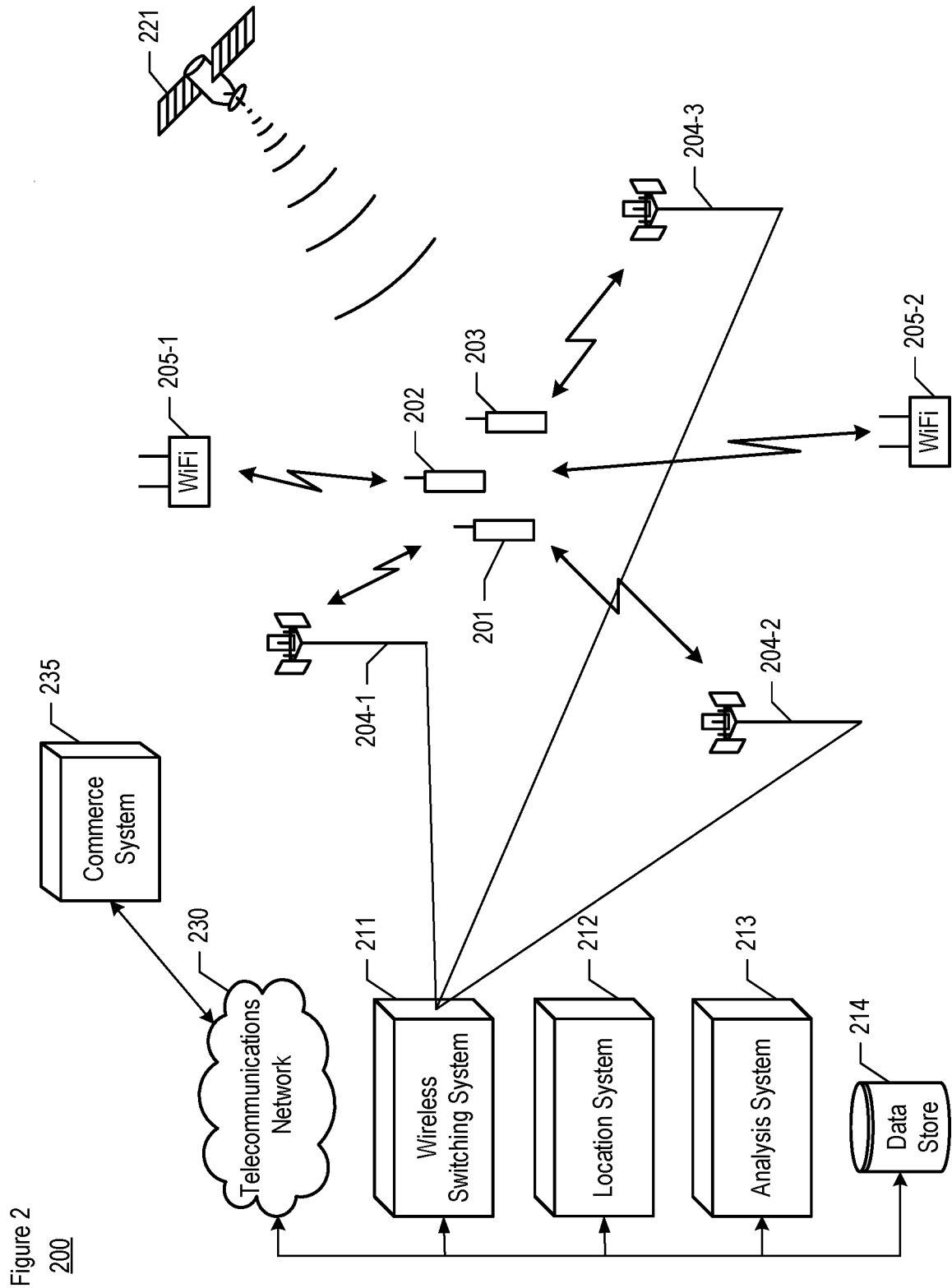
FIG. 2 depicts a diagram of the salient components of wireless telecommunications system 200 in accordance with the illustrative embodiment.

FIG. 2 depicts a diagram of the salient components of wireless telecommunications system 200 in accordance with the illustrative embodiment of the present invention. System 200 comprises: wireless terminals 201, 202, and 203, cellular base stations 204-1, 204-2, and 204-3, Wi-Fi base stations 205-1 and 205-2, wireless switching system 211, location system 212, geo-temporal analysis system 213, Global Positioning System (GPS) constellation 221, location system 212, geo-temporal analysis system 213, and data store 214, which are interrelated as shown.

Wireless telecommunications system 200 provides wireless telecommunications service to all wireless terminals within its coverage area; in addition, geo-temporal analysis system 213 performs and coordinates the operations as described in more detail below. External systems can also be connected to geo-temporal analysis system 213 via telecommunications network 230 but are not expressly depicted in FIG. 2, e.g., a facial recognition system, a GPS tracking system, a credit reporting system, a roadway-traffic camera system, a roadway toll-booth system, etc., without limitation.

Wireless switching system 211, location system 212, analysis system 213, data store 214, cellular base station 204-1, 204-2, and 204-3, Wi-Fi base stations 205-1 and 205-2, telecommunications network 230, and commerce system 235 are all connected to one or more interconnected computer networks (e.g., the Internet, a local-area network, a wide-area network, etc.) and, as such, can exchange data.

Wireless terminals 201, 202 and 203 are devices that are capable of providing bi-directional voice, data, and video telecommunications services to their respective users, who are also known as "subscribers." Each wireless terminal comprises the hardware and software necessary to perform the tasks disclosed herein. Furthermore, each wireless terminal is mobile and can be at any location within a geographic region at any time.

Wireless terminal 201, 202 and 203 can perform at least some of the processes described below and in the accompanying figures. For example and without limitation, wireless terminal 201, 202 and 203 are capable of:

i. receiving one or more radio signals transmitted by cellular base stations 204-1, 204-2, and 204-3, Wi-Fi base stations 205-1 and 205-2, and GPS constellation 121, and ii. identifying each radio signal transmitted by cellular base stations 204-1, 204-2, and 204-3, Wi-Fi base stations 205-1 and 205-2, and GPS constellation 221, and of transmitting the identities of those signals, or information related to the identity of those signals, to location system 212, and iii. measuring one or more location-dependent traits of each radio signal transmitted by cellular base stations 204-1, 204-2, and 204-3, Wi-Fi base stations 205-1 and 205-2, and GPS constellation 221, and of transmitting the measurements to location system 212, and iv. estimating lateral location x-y and elevation z, based on one or more of the received and/or measured radio signals, and v. measuring the temperature and barometric pressure at wireless terminal 201 and transmitting those measurements to location system 212, and vi. exchanging signals (e.g., Bluetooth, etc.) with one other, and vii. transmitting one or more signals to cellular base stations 204-1, 204-2, and 204-3, Wi-Fi base stations 205-1 and 205-2 in accordance with specific parameters (e.g., signal strength, frequency, coding, modulation, etc.), and of transmitting those parameters and estimated location to location system 212, and viii. transmitting one or more signals to cellular base stations 204-1, 204-2, and 204-3, Wi-Fi base stations 205-1 and 205-2, including reports of telecommunications events experienced by the respective wireless terminal.

Illustrative examples of telecommunications events that are experienced and reported by wireless terminals 201, 202, and 203 include without limitation:

i. an origination of a voice call by the wireless terminal, ii. a receiving of a voice call by the wireless terminal, iii. an establishment of a voice call between the wireless terminal in the wireless network and another telecommunications terminal, whether in the network or elsewhere, i.e., establishing a call connection, iv. an origination of a Short Message Service ("SMS") message by the wireless terminal, v. a receiving of an SMS message by the wireless terminal, vi. an origination of a text message by the wireless terminal, vii. a receiving of a text message by the wireless terminal, viii. a location update request that is transmitted by the wireless terminal to an element of the network infrastructure, ix. an origination by the wireless terminal of an Unstructured Supplementary Service Data ("USSD") session, x. an origination of a data session by the wireless terminal, xi. an ending of a data session by the wireless terminal, xii. an activation, for the wireless terminal, of a packet data protocol ("PDP") context by a GPRS Support Node in the wireless network, xiii. a deactivation, for the wireless terminal, of a packet data protocol ("PDP") context by a GPRS Support Node in the wireless network, xiv. the wireless terminal attaching to a packet radio data network in the wireless network, and xv. the wireless terminal detaching from the packet radio data network in the wireless network.

Telecommunications-event records are generated (as described below) that report on the above-listed telecommunications events, wherein each record also comprises geo-temporal data associated with the telecommunications event. It will be clear to those having ordinary skill in the art how to recognize and implement the corresponding terms, if any, for non-3GPP types of wireless networks.

Wireless terminal 201, 202 and 203 provide the aforementioned telecommunications services to their respective users and perform the aforementioned tasks. It will, however, be clear to those skilled in the art, after reading this disclosure, how to make and use embodiments of the present invention in which wireless terminal 201, 202 and/or 203 provide a different set of services or perform a different set of tasks.

Wireless telecommunications service is provided to wireless terminals 201, 202, and 203 in accordance with both the Long-Term Evolution (LTE) 4G air-interface standard of the $3^{rd}$ Generation Partnership Project ("3GPP") and the WiFi standard. After reading this disclosure, however, it will be clear to those skilled in the art how to make and use alternative embodiments of the present invention that operate in accordance with one or more other air-interface standards (e.g., a 5G standard, a standard under development, a different 4G standard, Global System Mobile "GSM," UMTS, CDMA-2000, IS-136 TDMA, IS-95 CDMA, 3G Wideband CDMA, other IEEE 802.11 or wireless LAN standard, 802.16 WiMax, Bluetooth, etc.) in one or more frequency bands.

Wireless terminals 201, 202, and 203 receive precise location data from one or more satellites in GPS constellation 221. As those who are skilled in the art will appreciate after reading this specification, wireless terminal 201, 202 and/or 203 can use technologies other than GPS for location purposes in some other embodiments of the present invention. As those who are skilled in the art will also appreciate after reading this specification, wireless terminal 201, 202 and/or 203 can use a Global Navigation Satellite System (GNSS) other than GPS for location purposes, such as GLONASS, Galileo, Beidou, and other regional systems, for example and without limitation.

Although the illustrative embodiment depicts wireless telecommunications system 200 as comprising three wireless terminals, it will be clear to those skilled in the art, after reading this disclosure, how to make and use alternative embodiments of the present invention that comprise any number of wireless terminals.

Cellular base stations 204-1, 204-2, and 204-3 comprise the hardware and software necessary to be Long-Term Evolution (LTE) 3GPP-compliant and to perform the processes described below and in the accompanying figures. In some alternative embodiments of the present invention, base stations 204-1, 204-2, and 204-3 communicate in accordance with a different cellular standard. Each of cellular base stations 204-1, 204-2, and 204-3 are capable of continually, for example and without limitation:

i. receiving one or more radio signals transmitted by wireless terminals 201, 202, and 203, and ii. identifying each radio signal transmitted by wireless terminal 201, 202, and 203, and of transmitting the identities of those signals to location system 212, and iii. measuring one or more location-dependent traits of each radio signal transmitted by wireless terminal 201, 202, and 203, and of transmitting the measurements to location system 212, and iv. detecting and reporting on one or more of the telecommunications events occurring at wireless terminals 201, 202, and 203, and v. transmitting one or more signals to wireless terminal 201, 202, and 203 in accordance with specific parameters (e.g., signal strength, frequency, coding, modulation, etc.), and of transmitting those parameters to location system 212, and vi. broadcasting one or more signals that wireless terminals can use for various purposes (e.g., mobile assisted handoff, location determination, etc.).

Wi-Fi base stations 205-1 and 205-2 communicate with wireless terminal 201, 202, and 203 via radio and in accordance with a WiFi protocol. Wi-Fi base stations are also commonly referred to by a variety of alternative names such as access points, nodes, network interfaces, and so forth. In some alternative embodiments of the present invention, base stations 205-1 and 205-2 communicate in accordance with a different IEEE 802.11 standard or wireless LAN standard entirely. Wi-Fi base stations 205-1 and 205-2 are terrestrial, immobile, and within a geographic region. Although the illustrative embodiment comprises two Wi-Fi base stations, it will be clear to those skilled in the art, after reading this disclosure, how to make and use alternative embodiments of the present invention that comprise any number of Wi-Fi base stations.

Each of Wi-Fi base stations 205-1 and 205-2 are capable of continually:

i. receiving one or more radio signals transmitted by wireless terminal 201, 202, and 203, and ii. identifying each radio signal transmitted by wireless terminal 201, 202, and 203, and of transmitting the identities of those signals to location system 212, and iii. measuring one or more location-dependent traits of each radio signal transmitted by wireless terminal 201, 202, and 203, and of transmitting the measurements to location system 212, and iv. detecting and reporting on one or more of the telecommunications events occurring at wireless terminals 201, 202, and 203, and v. transmitting one or more signals to wireless terminals 201, 202, and 203 in accordance with specific parameters (e.g., signal strength, frequency, coding, modulation, etc.), and of transmitting those parameters to location system 212, and vi. broadcasting one or more signals that wireless terminals can use for various purposes (e.g., mobile assisted handoff, location determination, etc.).

Wireless switching system 211 comprises a switch that orchestrates the provisioning of telecommunications service to wireless terminals 201, 202, and 203 and the flow of information to and from location system 212, and geo-temporal analysis system 213, and data store 214, as described below and in the accompanying figures. As is known to those skilled in the art, wireless switches are also commonly referred to by other names such as wireless switching centers, mobile switching centers, mobile telephone switching offices, routers, and so on.

Wireless switching system 211 collects data from throughout wireless telecommunications system 200, including telecommunications events reports that are reported by wireless terminals and/or by base stations, and generates telecommunications-event records according to the telecommunications events that are listed above, without limitation. Illustratively, wireless switching system 211 collects location data from location system 212, from the base stations, and from wireless terminals 201, 202, and 203. Each telecommunications-event record generated by wireless switching system 211 associates the reported-on telecommunications event with a geo-temporal datum that indicates a location and time at which the reported-on telecommunications event is estimated to have occurred. Wireless switching system 211 transmits the telecommunications-event records to geo-temporal analysis system 213 and to data store 214.

It will be clear to those having ordinary skill in the art, after reading this disclosure, how to make alternative embodiments wherein wireless switching system 211 is not the entity that generates the telecommunications-event records, and instead location system 212 generates these records; or location system 212 generates these records based at least in part on data gathered from probes; or a combination of system 211-generated and system 212-generated records; or the telecommunications-event records are generated by another system whether part of or outside of system 200, and are made available to geo-temporal analysis system 213 for processing and analysis as described in further detail below.

Location system 212 comprises hardware and software that estimates one or more locations for wireless terminals 201, 202, and 203, or maintains the location estimates if provided from somewhere else, such as the wireless terminals. Location system 212 provides geo-temporal data that is to be incorporated into telecommunications-event records, and further provides real-time geo-temporal data on-demand, e.g., when geo-temporal analysis system 213 so requests. The location system estimates a location that is associated with telecommunications events, including events other than call origination and call termination—events such as location area updates, powering on, powering off, etc. Location system 212 provides location capabilities across 2G (GSM/CDMA), 3G (UMTS/WCDMA), 4G (LTE), and 5G air interfaces, as well as indoor technologies such as Wi-Fi, DAS, and Femtocells. The location system enables the ability to simultaneously locate all subscribers in a wireless network in real-time and on a historical basis.

Geo-temporal analysis system 213 is a data-processing system that comprises hardware and software, and that is configured to perform the geo-temporal analysis according to the illustrative embodiment, including the generating of subscriber mobility profiles for one or more of wireless terminals 201, 202, and 203 based on location data obtained from location system 212. Geo-temporal analysis system 213 executes and coordinates the operations described herein in reference to method 400, including wherein geo-temporal analysis system 213 communicates with external systems that are not part of system 200.

Data store 214 is a digital data storage system that is responsible for receiving, storing, archiving, and retrieving data. Illustratively, data store 214 receives the results of the analysis performed by geo-temporal analysis system 213 and archives these results along with the various records and data received by geo-temporal analysis system 213.

Telecommunications network 230 is well known in the art and provides connectivity and telecommunications (voice and/or data) among the systems that connect to it, including geo-temporal analysis system 213, one or more commerce systems 235, and systems that are external to wireless telecommunications system 200 but are not shown in FIG. 2, e.g., a facial recognition system, a GPS tracking system, a credit reporting system, a roadway-traffic camera system, a roadway toll-booth system, etc., without limitation.

Commerce system 235 is well known in the art and is illustratively a banking system that telecommunicates with geo-temporal analysis system 213 (illustratively via telecommunications network 230) to transmit financial records to geo-temporal analysis system 213, including bank account transactions, credit card transactions, debit card transactions, deposits, debits, transfers of funds, and other records that associate a user and/or a wireless terminal with these transactions; the records also preferably comprise geo-temporal data for the reported-on transactions.

It will be clear to those having ordinary skill in the art, after reading the present disclosure, how to make and use alternative embodiments wherein geo-temporal analysis system 213 is incorporated into one of the other illustrated systems, e.g., location system 212, or wireless switching system 211. It will be further clear to those having ordinary skill in the art, after reading the present disclosure, how to make and use alternative embodiments wherein geo-temporal analysis system 213 further comprises one or more of the other illustrated systems, e.g., location system 212 and/or wireless switching system 211 and/or data store 214. It will be further clear to those having ordinary skill in the art, after reading the present disclosure, how to make and use alternative embodiments wherein geo-temporal analysis system 213 telecommunicates directly with one or more external systems without the intervening services of telecommunications network 230.

Figure 3:
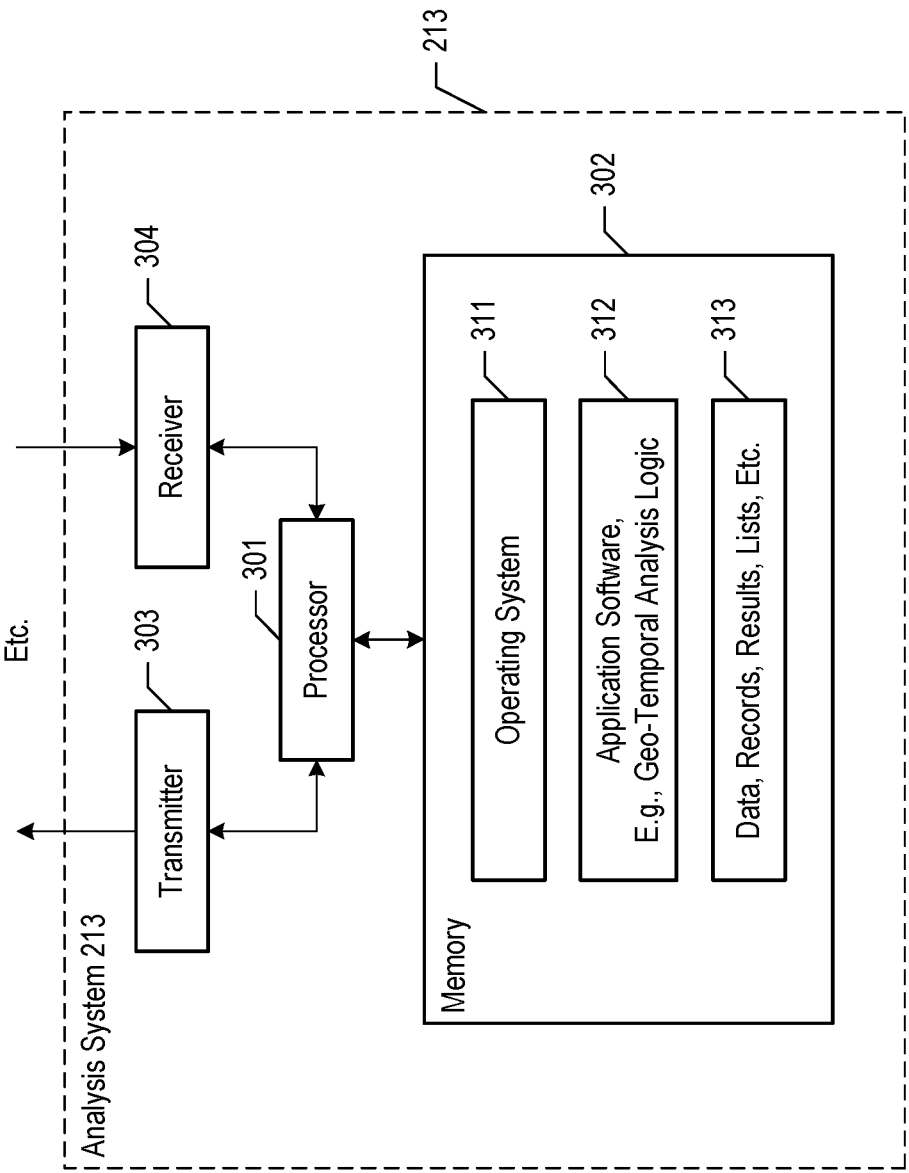
FIG. 3 depicts a block diagram of the salient components of geo-temporal analysis system 213.

FIG. 3 depicts a block diagram of the salient components of geo-temporal analysis system 213 in accordance with the illustrative embodiment. Analysis system 213 is a data-processing system that comprises: processor 301, memory 302, and transmitter 303 and receiver 304.

Processor 301 is a general-purpose processor that is well known in the art. Processor 301 can execute an operating system and the application software that performs at least some of the operations disclosed herein, including, but not limited to, those in FIG. 4. When operating in conjunction with the other components of analysis system 213, processor 301 executes the software, processes data, and telecommunicates according to the operations described herein.

Memory 302 is non-transitory and non-volatile computer memory technology that is well known in the art. Memory 302 stores operating system 311, application software 312, and element 313 which comprises data, records, results, lists, etc. It will be clear to those having ordinary skill in the art how to make and use alternative embodiments that comprise more than one memory 302; or subdivided segments of memory 302; or a plurality of memory technologies that collectively store operating system 311, application software 312, and element 313. The specialized application software 312 that is executed by processor 301 is illustratively denominated the "geo-temporal analysis logic" that enables geo-temporal analysis system 213 to perform the operations of method 400.

Transmitter 303 is a component that enables analysis system 213 to telecommunicate with other components internal and external to wireless telecommunications system 200 by transmitting signals thereto. For example, transceiver 303 enables telecommunication pathways to wireless switching system 211, location system 212, data store 214, etc. within system 200, as well as to other systems that are external to system 200, such as telecommunications network 230, a monitoring system, a tracking system, a commerce system, another wireless network, etc., without limitation. Transmitter 303 is well known in the art. It will be clear to those having ordinary skill in the art how to make and use alternative embodiments that comprise more than one transmitter 303.

Receiver 304 is a component that enables analysis system 213 to telecommunicate with other components internal and external to system 200 by receiving signals therefrom. For example, receiver 304 enables telecommunication pathways from wireless switching system 211, location system 212, data store 214, etc. within system 200, as well as from other systems that are external to system 200, such as telecommunications network 230, a monitoring system, a commerce system, a tracking system, another wireless network, etc., without limitation. Receiver 304 is well known in the art. It will be clear to those having ordinary skill in the art how to make and use alternative embodiments that comprise more than one receiver 304.

It will be clear to those skilled in the art, after reading the present disclosure, that in alternative embodiments the data-processing hardware platform of geo-temporal analysis system 213 can be embodied as a multi-processor platform, as one or more servers, as a sub-component of a larger computing platform, or in some other computing environment. It will be clear to those skilled in the art, after reading the present disclosure, how to make and use the data-processing hardware platform for geo-temporal analysis system 213.

Figure 4:
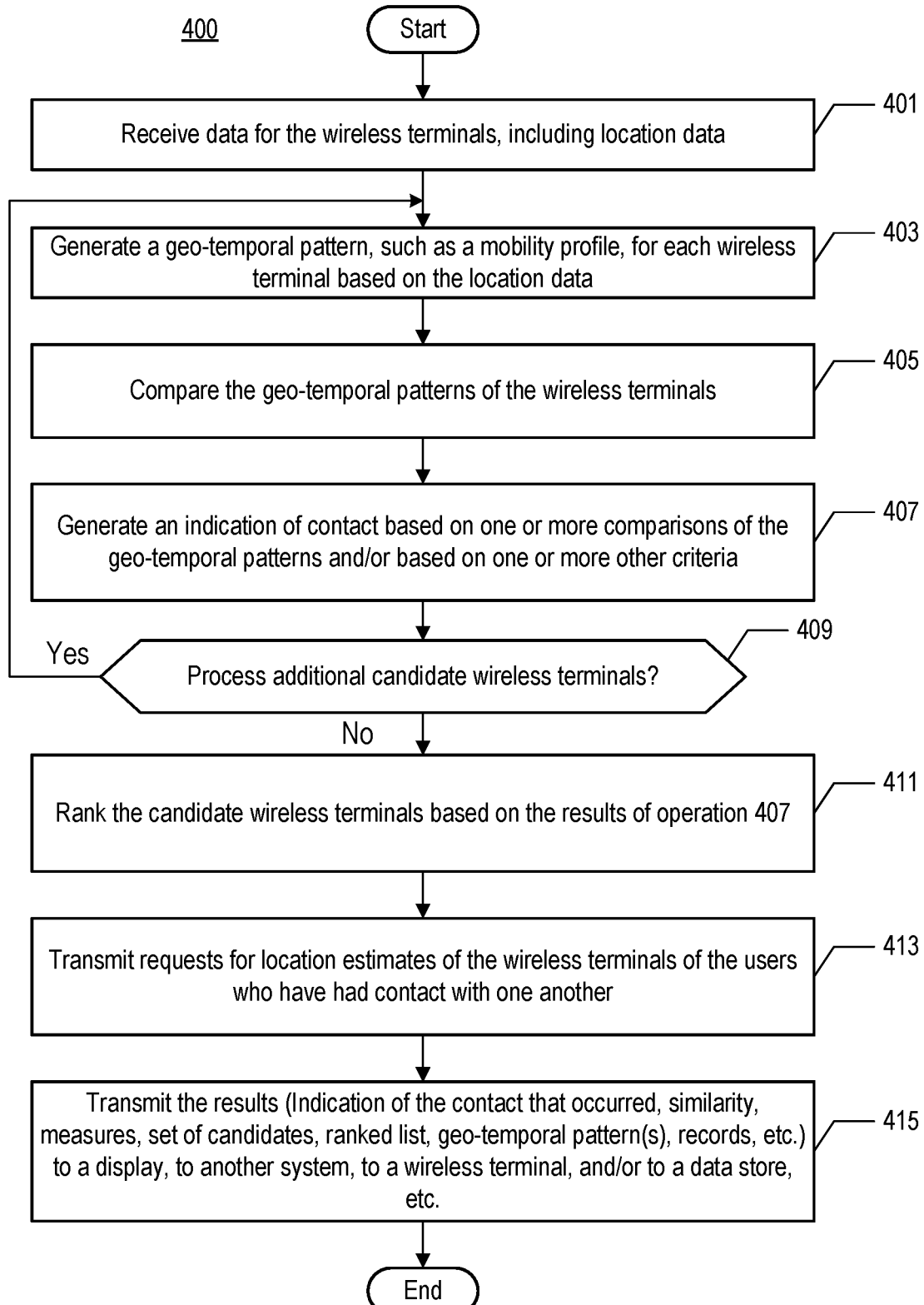
FIG. 4 depicts a flowchart of the salient operations of method 400 according to the illustrative embodiment.

FIG. 4 depicts a flowchart of the salient operations of method 400 according to the illustrative embodiment. FIG. 4 and the corresponding text describe a technique for determining that a first user of a first wireless terminal has come into contact with a second user of a second wireless terminal, wherein the second user has been diagnosed with a particular disease. The figure and corresponding text also describe a technique for determining whether a first user of a first wireless terminal is an index case of a disease that both a second user of a second terminal and a third user of a third terminal are diagnosed as having. As those who are skilled in the art will appreciate after reading the specification, the operations disclosed herein can be adapted for other purposes as well.

Illustratively, the first user is the user of wireless terminal 201, the second user is the user of wireless terminal 202, and the third user is the user of wireless terminal 203, unless otherwise indicated, at least in the first iteration of the operations described below. Illustratively, the geo-temporal patterns that are generated and compared are in the form of mobility profiles, unless otherwise indicated. Illustratively, the mobility profiles that are compared are generated as needed and from geo-temporal data, but alternatively can be predetermined mobility profiles, or other forms of geo-temporal patterns, which have been generated in advance from geo-temporal data or through other means.

Geo-temporal analysis system 213 executes and coordinates the operations of method 400 in accordance with the illustrative geo-temporal analysis logic. It will be clear to those skilled in the art, after reading the present disclosure, how to make and use alternative embodiments of the disclosed methods wherein some of the disclosed operations are performed by other elements and/or systems. For example and without limitation, at least some of the operations disclosed as being performed by geo-temporal analysis system 213 can be performed by one or more of location system 212, terminals 201 through 203, and so forth.

It will also be clear to those having ordinary skill in the art, after reading the present disclosure, how to make and use alternative embodiments of method 400, and also of any other methods disclosed in this specification, wherein the recited operations sub-operations, and messages are differently sequenced, grouped, or sub-divided. It will also be clear to those skilled in the art, after reading the present disclosure, how to make and use alternative embodiments of the disclosed methods wherein some of the described operations, sub-operations, and messages are optional, or are omitted.

At operation 401, geo-temporal analysis system 213 receives data including geo-temporal location data records for each wireless terminal 201, 202, and 203, and for other wireless terminals. At least some of the data, including the location data, are identified by an identifier (e.g., IMSI, etc.) of each wireless terminal. The data includes records—of the location data and otherwise—of one or more candidate "contacts" and/or one or more infected persons, who are the users of the respective wireless terminals. Operation 401 is described in more detail in FIG. 5.

At operation 403, geo-temporal analysis system 213 filters the records to generate a geo-temporal pattern corresponding to each wireless terminal, based on one or more characteristics related to a disease being analyzed. In some embodiments of the present invention, a candidate contact's and/or infected person's geo-temporal pattern comprises a subscriber behavioral model of the person—that is, a "subscriber mobility profile" or "mobility profile." Operation 403 is described in more detail in FIG. 6.

In some embodiments of the present invention, geo-temporal analysis 213 initially filters the records to narrow down the wireless terminals to be analyzed—specifically to the specific wireless terminals for which geo-temporal patterns need to be generated. This initial filtering can be based on one or more characteristics related to the disease being analyzed. Insights as to what criteria might be used for this initial filtering can be found throughout this specification, including in FIG. 9. For illustrative purposes, system 213 narrows down the wireless terminals initially to wireless terminals 201, 202, and 203, although additional candidate wireless terminals can also be processed later (i.e., can take the place of terminal 201 for subsequent iterations of the operations described below).

At operation 405, geo-temporal analysis system 213 compares the geo-temporal patterns of the wireless terminals. In essence, system 213 compares the geo-temporal pattern of the candidate contact in the current iteration, with one or more geo-temporal patterns of the infected person or persons, by comparing the data related to the respective wireless terminals representing their users. Operation 405 is described in more detail in FIG. 8.

At operation 407, based on the comparing of the geo-temporal patterns of the wireless terminals at operation 405, geo-temporal analysis system 213 infers contact having occurred between the user of the candidate wireless terminal (e.g., the first wireless terminal) and one or more other users, and generates a corresponding indication of contact. Operation 407 is described in more detail in FIG. 10.

At operation 409, geo-temporal analysis system 213 determines whether to repeat operations 403 through 407 for each additional candidate wireless terminal, generating that additional candidate's geo-temporal pattern at the next iteration of operation 403, and comparing that candidate wireless terminal's geo-temporal pattern, at the next iteration of operation 405, to that of the second wireless terminal, and to that of the first wireless terminal as applicable. For example and without limitation, the users of the additional candidate wireless terminals might have been pre-screened as being possible contacts in regard to transmission of the disease being analyzed.

At operation 411, after one or more candidate wireless terminals have been analyzed, system 213 ranks the candidate wireless terminals (e.g., terminal 201, etc.) based on how closely each of their first geo-temporal patterns compares to the second, and possibly third, geo-temporal pattern—that is, of wireless terminals 202 and 203—and generates a corresponding ranked list of candidates. In accordance with the illustrative embodiment, a ranking is an assessment of the level of risk of infection for each candidate contact associated with a candidate wireless terminal. Depending on what method 400 is being used to analyze, the level of risk of infection can be in terms of either (i) a candidate wireless terminal's user having been infect by wireless terminal 202's user, or (ii) a candidate wireless terminal's user being the index case in regard to wireless terminal 202's and 203's users.

The ranking scheme can be based on the measures of closeness from operation 405 and the threshold checks in operation 407. Different sensitivity levels can be established in measuring closeness from one candidate wireless terminal to another (e.g., by applying different comparison result thresholds used in operation 407 for the different candidate wireless terminals, etc.), thus possibly yielding different outcomes in the ranking.

Ranking of one or more candidates can also be determined by the location itself of where contact has been determined to have occurred, wherein contact at one location, or type of location (e.g., indoor versus outdoor, immovable versus movable, etc.), might be ranked differently than another. The location itself might be immovable (e.g., a room, etc.) or might be movable (e.g., a vehicle, etc.).

At operation 413, and based on the results of operations 407 and/or 411, geo-temporal analysis system 213 transmits (e.g., to location system 212, etc.) one or more requests for location estimates of at least one of the first, second, and third wireless terminals, to one or more terminals of the ranked contacts, and/or to one or more terminals of ranked contacts above a predetermined ranking, in any combination. For example, analysis system 213 transmits a mobile terminated location request (MT-LR), as is known in the art. The location request, and the respective location estimate that is received by geo-temporal analysis system 213 in response, enable an investigator to begin tracking or surveilling, for example, the infected person's wireless terminal.

At operation 415, geo-temporal analysis system 213 transmits the indication of contact, the measures of closeness, the set(s) of candidate contacts, the ranking of contact candidates, an indication of the inferred contact that occurred, and/or any other information determined in one or more of the aforementioned operations in FIG. 4, to a display, to another system, to a wireless terminal, and/or to a data store, etc., without limitation. Illustratively, geo-temporal analysis system 213 transmits some or all of the foregoing information to an external monitoring system operated by public health authorities, and also to data store 214.

Geo-temporal analysis system 213 also archives the records and other data that formed the basis for operations 401 through 413 to data store 214.

Figure 5:
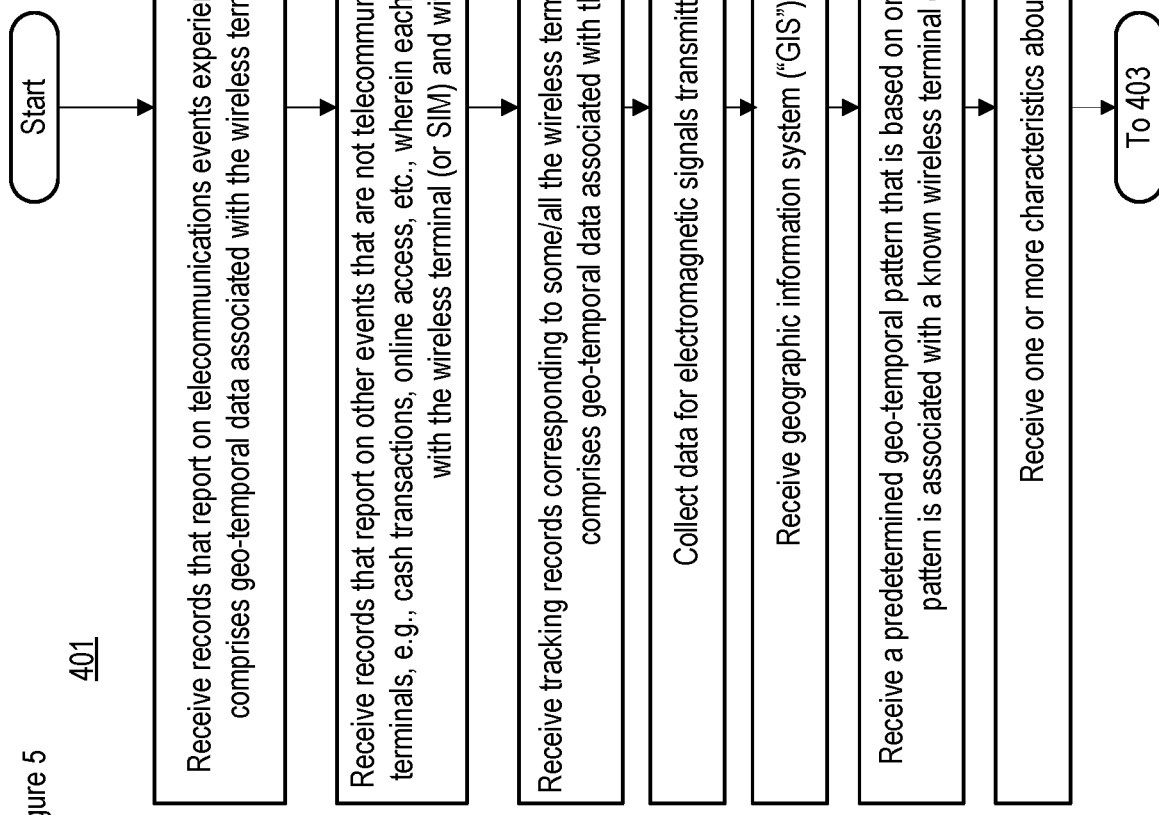
FIG. 5 depicts a flowchart of the salient sub-operations of operation 401.

FIG. 5 depicts a flowchart of the salient sub-operations of operation 401, in which geo-temporal analysis system 213 receives data about wireless terminals 201, 202, and 203, including location data.

At operation 501, geo-temporal analysis system 213 receives records that report on telecommunications events experienced by wireless terminals 201, 202, and 203, described earlier. Each record comprises geo-temporal data associated with the respective telecommunications event, illustratively a geo-temporal datum documenting the location and point in time that the telecommunications event is estimated to have occurred (e.g., a record wherein the wireless terminal received a call at a location $L_1$ at time $T_1$, etc.).

Illustratively, these records are generated by and received from wireless switching system 211, but in alternative embodiments, these records are received from another element of system 200, e.g., location system 212, are received from an external system, or are generated by geo-temporal analysis system 213, or a combination of one or more of these sources of records. As noted earlier, any number of telecommunications events are recorded and reported on in corresponding telecommunications-event records that are associated with the given wireless terminal.

At operation 503, geo-temporal analysis system 213 receives records that report on other events that are not telecommunications events that occurred at the wireless terminal, wherein each record comprises geo-temporal data associated with the respective event, illustratively a geo-temporal datum documenting the location and point in time that the event is estimated to have occurred (e.g., a record wherein the wireless terminal was used to conduct a financial transaction at a location $L_2$ at time $T_2$, e.g., a purchase, a refund, a deposit, a transfer of funds, a credit card transaction, a debit card transaction, etc.).

Illustratively, these records are received from one or more commerce systems 235 and/or from an element of system 200 that provides telecom service, e.g., a base station, as appropriate. It will be clear to those having ordinary skill in the art, after reading the present disclosure, how to record and report on any number of events, and further how to collect, construct, generate, and/or receive any number of corresponding non-telecommunications-event records.

At operation 505, geo-temporal analysis system 213 receives tracking records, including associated geo-temporal data (e.g., a record wherein the wireless terminal was at a location $L_3$ at time $T_3$, etc.), corresponding to at least some of the wireless terminals in system 200, e.g., GPS-based and/or other GNSS-based location records of latitude, longitude, and/or elevation, video records, monitoring (e.g., surveillance, etc.) records, roadway-traffic camera records, toll-booth records, etc. without limitation from an appropriate system (e.g., location system 212, Foursquare, Google, Facebook, etc.).

It will be clear to those having ordinary skill in the art, after reading the present disclosure, how to record, collect, construct, generate, and/or receive—and process if necessary—the records recited in the present operation such that each record is associated with a particular user and/or wireless terminal (e.g., a record that associates a user's wireless terminal with a pass through a toll booth, a record that associates a user's wireless terminal with being in a particular monitored geographical area, etc.).

At operation 507, geo-temporal analysis system 213 collects data (e.g., round-trip times, signal strengths, wireless terminal identifiers, types of messages exchanged, etc.) for electromagnetic signals (e.g., radio signals, etc.) transmitted between each pair of wireless terminals 201, 202, and 203. System 213 also collects or determines time information (e.g., timestamps, etc.) as to when each signal transmission occurred.

At operation 509, geo-temporal analysis system 213 receives data from a Geographic Information System ("GIS") that is well known in the art, and/or from a similar source of electronic maps. The received data comprises electronic maps and information about the terrain covered by wireless telecommunications system 200, for example indicating where there are water surfaces, parks, streets, buildings, etc. This information can be correlated to the geo-temporal data to develop, generate, and analyze geo-temporal patterns that comprise useful additional attributes, such as indoor/outdoor attributes, etc.

At operation 511, geo-temporal analysis system 213 receives a predetermined geo-temporal pattern of an infected person, such as a predetermined mobility profile. As those who are skilled in the art will appreciate, after reading this specification, a predetermined pattern can be used instead of, or in addition to, one or more patterns generated as needed or on-the-fly.

At operation 513, geo-temporal analysis system 213 receives one or more characteristics (e.g., epidemiological factors, etc.) about one or more diseases with which the infected person is infected with.

After operation 513, control of task execution proceeds to operation 403.

Figure 6:
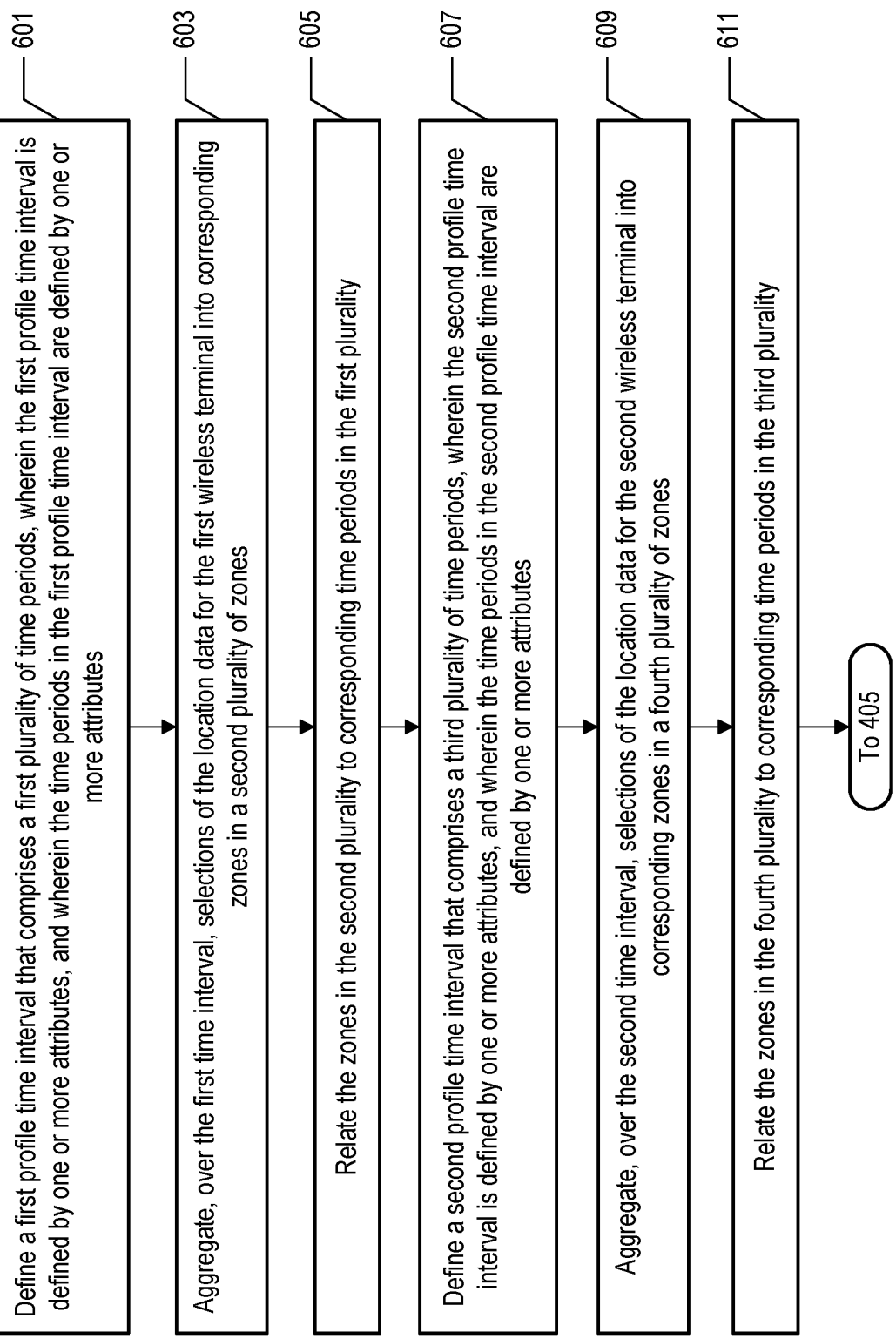
FIG. 6 depicts a flowchart of the salient sub-operations of operation 403.

FIG. 6 depicts a flowchart of the salient sub-operations of operation 403, in which geo-temporal analysis system 213 generates one or more geo-temporal patterns, such as mobility profiles.

For each candidate in the set of candidate wireless terminals, geo-temporal analysis system 213 generates a geo-temporal pattern that is based on data from those records that are associated with the respective candidate contact—and particularly on the geo-temporal attributes gleaned from those records. Depending on the particular implementation, only some of the records might be selected as the basis for generating the geo-temporal pattern.

Illustratively, the geo-temporal pattern is generated from analyzing a plurality of records for each candidate, gathered over a period of time such as one month, the plurality of records comprising one or more of the following without limitation:
  i. records that report on telecommunications events, as received in operation 501, and
  ii. records that report on other events that are not telecommunications events, as received at operation 503, and
  iii. tracking records, as received in operation 505, and
  iv. data about the signals exchanged directly between wireless terminals, as received in operation 507.

Illustrative examples of geo-temporal attributes include one or more of the following, alone or in combination, without limitation:

i. A location and a point in time, e.g., location $L_4$ at 10 am on Jul. 11, 2012, and
  ii. A location and a period of time, e.g., location $L_5$ from 9:30 to 10:30 am on Jul. 11, 2012, and
  iii. A location and a duration of time after arrival at that location, e.g., location $L_6$ from arrival time until departure from said location, and
  iv. A location and a duration of time when no calls are made or received on the wireless terminal at that location $L_7$.

It will be clear to those having ordinary skill in the art, after reading the present disclosure, how to define and use other geo-temporal attributes upon which a geo-temporal pattern can be based.

In some alternative embodiments of the present invention, a geo-temporal pattern of an infected person can be received or prepared in advance, in response to the person's health practitioner or other health care provider having contacted the proper health authority, which then has the geo-temporal records of the infected person released and/or the identifier (e.g., IMSI, etc.) of the infected person's wireless terminal or terminals, with which the geo-temporal pattern is created, including one or more subscriber mobility profiles.

In some embodiments of the present invention, records are filtered based on the empirical data collected in accordance with operation 507. For example, records can be kept based on the degree to which the empirical data for electromagnetic signals (e.g., radio signals, etc.) transmitted between two wireless terminals suggest that the wireless terminals have been proximate to each other, when the wireless terminals have been proximate, and for how long.

In addition to the records, geographic information—as received in operation 509—is also available for further analyzing a candidate contact's records. For example, location data from the records can be correlated or refined according to the geographic information to determine whether, for example, a location is known to be outdoors, e.g., a park, a lake, a street, or indoors, e.g., within the footprint of a high-rise building or a warehouse. A level of risk of infection can be assigned based on whether indoors or outdoors, and/or based on the particular type of location (e.g., a park, a building, etc.). For example, the level of risk can be lower if outdoors and higher if indoors, if an airborne mode of transmission applies.

Illustrative examples of geo-temporal patterns for a given wireless terminal include one or more of the following, alone or in any combination with one other, without limitation:
  i. the set of locations visited by the wireless terminal over a given period of time, and
  ii. the set of locations where the wireless terminal spends more than a certain amount of time, e.g., more than 30 minutes, and
  iii. the set of locations where the wireless terminal spends a certain amount of time, e.g., between 15 minutes and 75 minutes, and
  iv. the location of the wireless terminal at a certain point in time, e.g., noon, every weekday, and
  v. the relative location (e.g., proximity, etc.) of a first wireless terminal to a second wireless terminal at a certain point or points in time, and
  vi. the set of locations where a first wireless terminal is proximate to a second wireless terminal for more than a certain amount of time, e.g., more than 30 minutes.

The variety, granularity, periodicity, combinations, and complexity of geo-temporal patterns can vary based on the geo-temporal attributes defining the respective contact tracing. Also, the operative period of time for determining the geo-temporal pattern also will vary. The geo-temporal attributes to be considered in generating a geo-temporal pattern for the candidate contacts' wireless terminals can vary from one contact tracing to another, and from one wireless terminal and user to another.

In some embodiments of the present invention, geo-temporal patterns related to absolute location in space can be used to infer some types of information, such as a candidate contact's direct exposure to an infected place, previously visited by an infected person. Geo-temporal patterns related to location in relation to another wireless terminal can be used to infer some other types of information, such as a candidate contact's direct exposure to an infected person.

After the proper attributes (e.g., geo-temporal attributes and other attributes), operational period of time, and other relevant considerations are specified for a contact tracing according to the illustrative embodiment, geo-temporal analysis system 213 can use machine learning techniques that are well known in the art to generate the geo-temporal pattern for each candidate wireless terminal. It will be clear to those having ordinary skill in the art, after reading the present disclosure, how to make and use alternative embodiments wherein other techniques generate the geo-temporal pattern, or wherein a combination of machine learning and other techniques is used.

In accordance with the illustrative embodiment, geo-temporal analysis system 213 generates mobility profiles, which comprise a reduced set of data points sufficient to profile aspects of the wireless terminal's behavior and, with that, the corresponding user's behavior. In one aspect of the invention, wireless terminal locations collected over a period of time, of which there can be an infinite number of possible locations, are aggregated into a finite number of geographic zones.

For example, a subscriber (i.e., the wireless terminal user) lives in an apartment complex and works in a nearby office complex. The behavior pattern for the subscriber is made up of multiple call originations and SMS activity from within the apartment, further activity in the apartment complex common areas, and activity from a car nearby the apartment complex, all of which can be used, along with other records collected (e.g., GPS-based, etc.), to determine the subscriber's locations visited and times at the locations visited. The wireless terminal exhibits still further activity on the subscriber's work commute and then activity from different locations within the office complex.

In accordance with the illustrative embodiment, this location data is aggregated into a mobility profile where there are two zones, the apartment complex and the office campus, and possibly other zones as well (e.g., along the commuting route or routes, etc.). The geographic reach of a zone is not limited to a fixed location, nor must each zone cover equal area. According to the present invention, subscriber mobility profile zones are aggregated and stored in data store 214 accessible to geo-temporal analysis system 213.

Mobile profiles are illustrated in FIGS. 7A, 7B, and 7C, which depict exemplary mobility profiles 701, 702, and 703, respectively, for the subscribers of wireless terminals 201, 202, and 203. The exemplary mobility profiles span one calendar week of time interval; however, the mobility profiles need not coincide with one another in time. In general, the first profile time interval, second profile time interval, and third profile time interval might or might not overlap with one another. Further, the profile time interval covered in a given mobility profile is configurable.

The exemplary mobility profile time intervals further divide into days and hours, and consequently provide the subscribers' zone locations in 30-minute time periods over the course of week. The length of each time period is configurable and need not be the same as one another. Zones in this aspect of the invention are an aggregation of higher resolution locations that location system 212 may provide. The geographic scope of a zone is configurable, and the total number of locations considered in a zone aggregation is configurable. The person of ordinary skill in the art after reading this disclosure will know how many locations to consider in a zone aggregation. In this example, more than 500 location data points have been considered for each wireless terminal 201, 202, and 203. Furthermore, the number of data points aggregated into the different zones can vary and might or might not be the same from one zone to another.

Still referring to FIGS. 7A, 7B, and 7C, for any 30-minute time period, mobility profiles 701, 702, and 703 provide the zone location for respective wireless terminals 201, 202, and 203, if that data is available. In other words, it is possible that the wireless terminal was not locatable at a certain time, in which case no zone data would be available. Or it may be that the wireless terminal was locatable, but that the system had not aggregated a zone for the more specific location. In any case, FIG. 7B illustrates a lack of zone data with a blank for the time period, such as at gaps 708 and 710.

Consider, for example, the TUE column 706. It shows wireless terminal 202 located in Zone 6 until 8:00 PM. Between 8:00 AM and 8:30 AM, there is no zone data available, as denoted by gap 708. From 8:30 AM until at least 7:00 PM, mobility profile 702 indicates the presence of wireless terminal 202 in various zones.

Mobility profiles, including how some are generated and used, are further discussed in U.S. Pat. No. 10,560,839, which is incorporated by reference herein. In any event, it will be clear to those skilled in art, after reading the present disclosure, how to make and use mobility profiles 701, 702, and 703 as part of analysis system 213.

In some embodiments of the present invention, cluster analysis can be used to generate one or more mobility profiles defined by one or more of: clusters and clustering, uncertainty radius or radii, and entrance and/or exit times. In cluster analysis, for example, high-resolution location data is plotted on a map over a time interval, and the plots are analyzed for clusters over a predetermined area. A cluster of locations aggregates to a zone, such as a zone depicted in any of FIGS. 7A, 7B, and 7C. The zones may be standardized to shape and geographic area. Clustering can be used to identify "stay points," each of which being a separate place (e.g., "home", "workplace", etc.) where a person (e.g., an infected person, etc.) spends a significant amount of time as defined by an identified cluster.

In the example, system 213 can identify the plurality of clusters such that the clusters are representative of location of a person and are identified as a function of time. System 213 can perform a cluster analysis based on density-based clustering and, in particular, by using the data clustering algorithm "DBSCAN" as is known in the art. Cluster analysis is further discussed in U.S. Pat. Nos. 9,942,713 and 10,142,787, both of which are incorporated by reference herein.

In regard to generating a first mobility profile for wireless terminal 201, at operation 601 in FIG. 6, geo-temporal analysis system 213 defines a first profile time interval that comprises a first plurality of time periods, such as those referred to above and in regard to FIG. 7A. In some embodiments of the present invention, the first profile time interval and/or the time periods (e.g., their length or lengths, etc.) in the first profile time interval are defined by one or more attributes. One or more of the attributes can be based on a first disease that a second user is diagnosed as having, for example and without limitation. Specific characteristics of the first disease on which the one or more attributes can be based are described below.

At operation 603, geo-temporal analysis system 213 aggregates, over the first time interval, selections of the location data for the first wireless terminal into corresponding zones in a second plurality of zones. In aggregating the selections of the location data, system 213 forms or groups higher resolution locations, and possibly an infinite number of possible locations, into a finite number of geographic zones.

In some embodiments of the present invention, one or more characteristics of the zones (e.g., number of zones, size of each zone, shape of each zone, number of individual locations in a cluster aggregates to a zone, etc.) are defined by one or more attributes. One or more of the attributes can be based on a first disease that a second user is diagnosed as having, for example and without limitation. Specific characteristics of the first disease on which the one or more attributes can be based are described below.

At operation 605, geo-temporal analysis system 213 relates the zones in the second plurality to corresponding time periods in the first plurality. In relating the zones to the corresponding time periods, system 213 correlates the zones to times.

In generating a second mobility profile for wireless terminal 202, at operation 607, geo-temporal analysis system 213 defines a second profile time interval that comprises a third plurality of time periods, such as those referred to above and in regard to FIG. 7B. The first and second profile time intervals might or might not overlap each other. In some embodiments of the present invention, the second profile time interval and/or the time periods (e.g., their length or lengths, etc.) in the second profile time interval are defined by one or more attributes. One or more of the attributes can be based on a first disease that a second user is diagnosed as having, for example and without limitation. Specific characteristics of the first disease on which the one or more attributes can be based are described below.

At operation 609, geo-temporal analysis system 213 aggregates, over the second time interval, selections of the location data for the second wireless terminal into corresponding zones in a fourth plurality of zones. In some embodiments of the present invention, one or more characteristics of the zones (e.g., number of zones, size of each zone, shape of each zone, number of individual locations in a cluster aggregates to a zone, etc.) are defined by one or more attributes. One or more of the attributes can be based on a first disease that a second user is diagnosed as having, for example and without limitation. Specific characteristics of the first disease on which the one or more attributes can be based are described below.

At operation 611, geo-temporal analysis system 213 relates the zones in the fourth plurality to corresponding time periods in the third plurality.

After operation 611, control of task execution proceeds to operation 405.

The operations related to generating a first and second mobility profile are described above. Similar operations can be used to generate a third mobility profile for wireless terminal 203 and mobility profiles for additional wireless terminals. One or more of the attributes used to define a third mobility profile, and others, can be based on a first disease that a second user is diagnosed as having, for example and without limitation. Specific characteristics of the first disease on which the one or more attributes can be based are described below.

In regard to defining one or more mobility profile time intervals, as in accordance with operations 601 and 607, one of the relevant geo-temporal attributes might a specified point in time, wherein the point in time can be used to define a time interval. Accordingly, geo-temporal records that fall outside that time interval can be excluded from the mobility profile. The time interval, for example and without limitation, can be defined by (i) a start time of when the infected person is estimated to have become contagious and (ii) a stop time, if available, of when the infected person is estimated no longer to be contagious, wherein the start time and/or stop time can be adjusted as needed.

The mobility profile time intervals of interest that are described above and/or the time periods within each profile time interval and/or the zones, can be based on one or more characteristics of the disease being analyzed. For example, a profile time interval can be defined by one or more epidemiological factors received at operation 513, either alone or in combination with one another. These factors can be used to estimate when an infected person first became contagious and, if applicable, when the infected person is no longer contagious, wherein the window of contagiousness is relevant to defining a profile time interval. When the symptoms first appeared can be used to determine the start of contagiousness based on the particular disease. For example, chickenpox is infectious from two days before the spots appear. When the symptoms first appeared can also be used to determine the end of contagiousness based on the particular disease. For example, chickenpox is infectious until after the spots have crusted over, usually five days after the spots first appeared.

Similarly, viral load level(s) of a given disease of a person can be used to determine the time window of contagiousness. The viral load level is obtained from when a person is tested for a particular disease and is made available for purposes of contact tracing. Likewise, the level of antibodies in the tested person can be used to determine whether the person has recovered and/or whether the person has been infected in the past. Depending on the level of antibodies, along with knowing the particular type of disease involved, other information can be inferred such as the risk of the previously-infected person being infected again and, therefore, contagious again. Thus, it is possible that there might be more than one time window during which the infected person is contagious, which can affect which profile time interval or intervals are relevant in generating one or more mobility profiles, and which are not.

Similarly, the mode or modes of transmission (e.g., airborne, droplet, direct physical contact, indirect physical contact, fecal-oral, etc.) of a given disease can be used to determine the type of exposure needed in order for a candidate contact to be infected. The mode or modes of transmission can also be used to determine the lengths of one or more time periods in a plurality of time periods defined as part of a profile time interval. For example, a first mode of transmission might only require exposure to an infected person for a relatively short amount of time; accordingly, the length of a time period within a profile time interval might need to be decreased (e.g., to 15 minutes, to 5 minutes, etc.) in order to achieve sufficient accuracy when comparing mobility profiles. Conversely, a second mode of transmission might require exposure to an infected person for a relatively long amount of time; accordingly, the length of a time period within a profile time interval can be increased (e.g., to 60 minutes, etc.) with negligible or no loss in accuracy when comparing mobility profiles.

The surface lifespan/stability of a pathogen (i.e., a bacterium, virus, or other microorganism that can cause disease) can also be used to determine the risk of contagion and can be used to define one or more profile time intervals and/or the time periods within each profile time interval and/or zones. Additionally, the persistence of the pathogen can also be used to determine the risk of contagion and can be used to define one or more profile time intervals and/or the time periods within each profile time interval and/or zones. These characteristics are described in detail below and in regard to FIG. 8.

FIG. 8 depicts a flowchart of the salient sub-operations of operation 405, in which geo-temporal analysis system 213 compares the geo-temporal patterns of the different wireless terminals. This comparison can be accomplished in various ways, including but not limited to determining how closely each candidate contact's geo-temporal pattern matches the geo-temporal pattern of the infected person or persons—that is, how similar the patterns are to each other.

A comparison can account for one or more of the following considerations: (i) whether or not the infected person and a candidate contact were in proximity with each other at a location, (ii) whether or not the infected person and a candidate contact were at the same location as each other, but not necessarily at the same time, (iii) when the aforementioned events occurred, either in an absolute sense or relative to each other, and (iv) the length of time each event occurred for.

Geo-temporal analysis system 213 measures how closely each candidate's geo-temporal pattern matches the geo-temporal pattern of an infected person or persons. Geo-temporal analysis system 213 compares one geo-temporal pattern to another and evaluates a proper measure of closeness between them. The measure depends on the nature of the geo-temporal attributes in the geo-temporal patterns being compared. Some measures can be quantitative and some can be qualitative. For example, a first measure can be based on the locations (e.g., the types of locations, the particular locations, the number of locations) in which the infected person and candidate contact have been in proximity to each other. A second measure can be based on the locations that both infected person and candidate contact have visited (i.e., locations in common), but not necessarily at the same time. A third measure can be based on the length of time that the infected person and candidate contact are in proximity to each other. A fourth measure can be based on the length of time that the candidate contact is at a particular location previously visited by the infected person.

Additional measures of closeness can be based on: determining whether two people (e.g., infected person and candidate contact, etc.) are traveling together; determining whether two people are in the same residential building; determining whether two people are in the same office space; determining whether two people get in and/or out of a vehicle (e.g., bus, etc.) at the same place (e.g., bus stop, etc.). For instance, if (i) the two people are traveling together and (ii) get in and out of the same vehicle at the same place, then the measure of closeness of a match is higher than if (i) they are not traveling together or (ii) they get in a vehicle at different places or (iii) they get out of the vehicle at different places.

Two people traveling together can be inferred by looking either (i) at the locations and times within each respective geo-temporal pattern or (ii) at one or both geo-temporal patterns to see when a wireless terminal of the first person transmitted to a wireless terminal of the second person. Two people getting in or out of the same vehicle at the same time can be inferred by respectively comparing (i) when they first were proximate to each other to a GIS database (e.g., bus stops, etc.) or (ii) when they stopped being proximate to each other to said GIS database.

Additional measures of closeness can be based on assessing proximity between the respective first and second wireless terminals, resulting in an assessed proximity. In some embodiments of the present invention, assessed proximity is based, at least in part, on the data collected at operation 507 for electromagnetic signals transmitted between the first and second wireless terminals, including time information (e.g., timestamps, etc.) corresponding to the data for the electromagnetic signals. For example and without limitation, the time or times that signals were transmitted directly between two wireless terminals can be used to determine how long two wireless terminals—and, therefore, two users—were proximate in space to each other. Also, the times can be used to determine whether the two wireless terminals were proximate in space to each other during a time window when an infected person was contagious.

For example, if the two wireless terminals exchange Bluetooth signals, then the respective users must have come within Bluetooth range of each other and, consequently, were closer to each other than if the two terminals were out of Bluetooth range. Generally, the proximity of two wireless terminals—and, correspondingly, of an infected person and candidate contact—can be gauged based on the range of signal reception of the technology being used for direct terminal-to-terminal communication (i.e., electromagnetic signals directly transmitted between two wireless terminals).

As those who are skilled in the art will appreciate, after reading this specification, the range of signal reception of other technologies (e.g., WiFi Direct, D2D, near-field communication [NFC], etc.) can be used. For example, In Release 12 in the 3GPP specifications (incorporated by reference herein), ProSe (Proximity Services) is a D2D (Device-to-Device) technology that allows LTE devices to detect each other and to communicate directly. ProSe relies on multiple enhancements to existing LTE standards including new functional elements and a "sidelink" air interface for direct connectivity between devices.

The surface lifespan/stability of a pathogen (i.e., a bacterium, virus, or other microorganism that can cause disease) can be used to determine the risk of contagion and, therefore, can be used as another measure of closeness. A particular pathogen might live/persist on a first type of surface (e.g., cardboard, etc.) for a first length of time (e.g., 24 hours, etc.), while a different pathogen might live/persist on a second type of surface (e.g., plastic, etc.) for a second length of time (e.g., 3 days, etc.). In particular, analysis system 213 determines closeness by determining (i) how long after the infected person visited the location did the candidate contact visit the same location and (ii) whether the pathogen was still infectious at the time the candidate contact visited the location.

The surface lifespan/stability of a pathogen at a particular location can be assumed (e.g., worst case of 4 days, etc.) or estimated. Analysis system 213 can estimate the lifespan by estimating the type of surface at a location. For example, a parcel distribution center might have predominantly cardboard surfaces (i.e., on the shipping boxes), while an office complex might tend to have hard or shiny surfaces (e.g., metal, plastic, etc.); information about a particular location (e.g., zoning, type of business, etc.) can be found in the GIS or other type of database. Once the type of surface is estimated, the lifespan corresponding to that type of surface can be cross-referenced.

The persistence of a pathogen can be also related to whether the location is indoors or outdoors. For example, an airborne pathogen can dissipate more quickly outdoors than indoors. Accordingly, analysis system 213 can determine closeness in a match between infected person and candidate contact by determining (i) how long after the infected person visited the location did the candidate contact visit the same location and (ii) whether the pathogen dissipated sufficiently because the location was outdoors instead of indoors. Alternatively, an effective dissipated time can be assigned based on whether the location is outdoors or indoors. Additionally, the wind conditions can be considered if the location is outdoors, and ventilation conditions can be considered if the location is indoors.

In regard to the persistence of a pathogen within a particular environment and location, the time window of the persistence (e.g., a second time window, etc.) can be managed as a separate time window than the time window that an infected person is contagious (e.g., a first time window, etc.).

These illustrative examples are presented here for clarity. As noted, a proper measure of closeness depends closely on the nature of the relevant geo-temporal attributes and is specific to the details of the contact tracing and the data that are available to the geo-temporal analysis system. For example, the investigator might have information that suggests that a known infected person makes one or more visits to a particular location; if there are multiple, if inaccurate, estimates that a candidate contact visited the same location, the superposition of these multiple estimates leads toward a higher confidence that the infected person and candidate contact were at the same location.

In regard to comparing two mobility profiles, FIGS. 7A, 7B, and 7C also illustrate mobility profile matching in accordance with the illustrative embodiment. As per mobility profile 701 in FIG. 7A, on Sunday ("SUN") wireless terminal 201 remains in the same zone (i.e., Home Zone 1) for the day. On Monday ("MON") morning, wireless terminal 201 moves during its user's commute to Zone 3, then Zone 4, and then Zone 5, arriving at Office Zone 2 at about 9:30 AM. Wireless terminal 201 remains there until about 3:00 PM, when the wireless terminal's user commutes home to Zone 1 via Zones 5, 4, and 3. Mobile profile 701 also includes the locations and movements of terminal 201 for Tuesday through Saturday as well. This mobility profile is consistent with a person moving between their home and their place of work during the week, and staying at home on the weekend.

Meanwhile, wireless terminal 202's mobility profile 702 in FIG. 7B represents the wireless terminal's zone locations over the same time interval. As per mobility profile 702, on Sunday ("SUN") wireless terminal 202 remains in the same zone (i.e., Home Zone 6) for the day. On Monday ("MON") morning, wireless terminal 202 moves during its user's commute to Zone 3, then Zone 4, and then Zone 8, arriving at Office Zone 7 at about 9:30 AM. Wireless terminal 202 remains there until about 3:30 PM, when the wireless terminal's user commutes home to Zone 6 via Zones 8, 4, and 3. Mobile profile 702 also includes the locations and movements of terminal 202 for Tuesday through Saturday as well.

Lastly, wireless terminal 203's mobility profile 703 in FIG. 7C represents the wireless terminal's zone locations over the same time interval. As per mobility profile 703, on Sunday ("SUN") wireless terminal 203 remains in the same zone (i.e., Home Zone 9) for the day. On Monday ("MON") morning, wireless terminal 203 moves during its user's commute to Zone 10 and then Zone 11, arriving at Office Zone 2 at about 9:30 AM. Wireless terminal 203 remains there until about 5:00 PM, when the wireless terminal's user commutes home to Zone 9 via Zones 11 and then 10. Mobile profile 703 also includes the locations and movements of terminal 203 for Tuesday through Saturday as well.

In a profile-matching algorithm of the illustrative embodiment, analysis system 213 totals points based, at least in part, on the number of matching zones between the wireless terminals' respective mobility profiles. In this exemplary case described above, in terms of the zones in which their users are both present during the same time periods, mobility profile 701 for terminal 201 and mobility profile 702 for terminal 202 match each other in eight different respective time periods (i.e., between the two profiles) during the week: in Zones 3 and 4 on Monday between 8:00 and 9:00 AM, on Tuesday between 4:00 and 5:00 PM, and on Wednesday and Thursday between 8:00 and 9:00 AM.

Meanwhile, in terms of the zones in which their users are both present during the same time periods, mobility profile 701 for terminal 201 and mobility profile 703 for terminal 203 match each other in 60 different respective time periods during the week: all in Zone 2 (i.e., the place of work for both users 1 and 3) on Monday 11 times, on Tuesday 9 times, on Wednesday 15 times, on Thursday 14 times, and on Friday 11 times.

In comparing mobility profiles 702 for terminal 202 of the second user and 703 for terminal 203 of the third user, it can be seen that there are no zones in which the users are both present during the same time periods, nor do the users visit any of the same zones throughout the entire profile time intervals of interest. Thus, if both the second and third users are infected, it is probably not the case that one infected the other. But it is possible that the first user (as the index case) infected both the second and third user, as shown in the analysis that follows.

Based on the number of matching zones in which the users are both present during the same time periods, users 1 and 3 have a greater number of matches than users 1 and 2, resulting in a larger comparison result. Thus, based on matches in same respective time periods alone, it would appear that user 1 is at greater risk from infected user 3 than from infected user 2, assuming that the purpose of the analysis is to assess user 1's risk of exposure to the disease.

Additionally, the various measures of closeness described earlier can be applied to the foregoing point-scoring algorithm, in order to generate a comparison result. For example, if the window of contagiousness has not already been accounted for in defining the mobility profile intervals, the number of matching zones might be less than described above in regard to risk of contagion. Accordingly, the number of matching zones between users 1 and 3 can be reduced because user 3 is not contagious throughout the entire week. As another example, the risk of contagion in Zone 2 (e.g., a well-ventilated office complex, etc.) might be known in advance to be less than that somewhere else; accordingly, the number of matching zones between users 1 and 3 can be reduced. As yet another example, the surface stability and/or persistence of the pathogen might be long enough so that zone matches between time period in a first profile and a time period that is offset in a second profile need to be considered; accordingly, there are additional matches between users 1 and 2 based on their similar, but not identical, commuting patterns through Zones 3 then 4 in the morning and Zones 4 then 3 in the afternoon, in which users 1 and 2 are present in some of the same zones, but at slightly different times.

Additionally, the measure of closeness pertaining the wireless terminal exchanging electromagnetic signals described earlier can also be applied to the foregoing point-scoring algorithm, in order to generate a comparison result. For example, additional points can be applied based on whether radio signals (e.g., Bluetooth, etc.) are transmitted directly between the wireless terminals of interest, within those zones in which their users are both present during the same time periods, and can also be based on factors related to the transmissions, such as received signal strength and timing.

As those having ordinary skill in the art will appreciate after reading this specification, the profile-matching algorithm can be configured with a different point totaling system. Also, the point values associated with each condition that is met can be selected to suit the particular purpose of the implementation. Likewise, the mobility profile matching algorithm can be applied to different types of zones, to longer or shorter profile time intervals, and/or to longer or shorter time periods.

As part of performing the comparing of mobility profiles 701 and 702 as described above, at operation 801 geo-temporal analysis system 213 defines respective time periods between the first plurality of time periods for the first wireless terminal and the third plurality of time periods for the second wireless terminal. In other words, the individual time periods whose zones are to be compared across the mobility profiles, are defined. The respective time periods might or might not coincide in absolute time.

At operation 803, geo-temporal analysis system 213, for each of the respective time periods, compares a first zone (e.g., "Zone 1", "Zone 2", etc.) visited by the first wireless terminal in the second plurality of zones and a second zone (e.g., "Zone 1", "Zone 2", etc.) visited by the second wireless terminal in the fourth plurality of zones.

At operation 805, geo-temporal analysis system 213 generate a first comparison result based, at least in part, on the comparing of the first and second zones. For example and without limitation, the value of the first comparison result might be based on how many matches are found to be present for all of the respective time periods whose zones are compared, between the first and second mobility profiles.

The operations related to comparing a first and second mobility profile are described above. Similar operations can be used to compare the first and/or second mobility profile and a third mobility profile for wireless terminal 203 (i.e., mobility profile 703). Accordingly, at operation 807 geo-temporal analysis system 213 generates a second comparison result involving the first wireless terminal and the third wireless terminal. For example and without limitation, the value of the second comparison result might be based on how many matches are found to be present for all of the respective time periods whose zones are compared, between the first and third mobility profiles.

After operation 807, control of task execution proceeds to operation 407.

Figure 9:
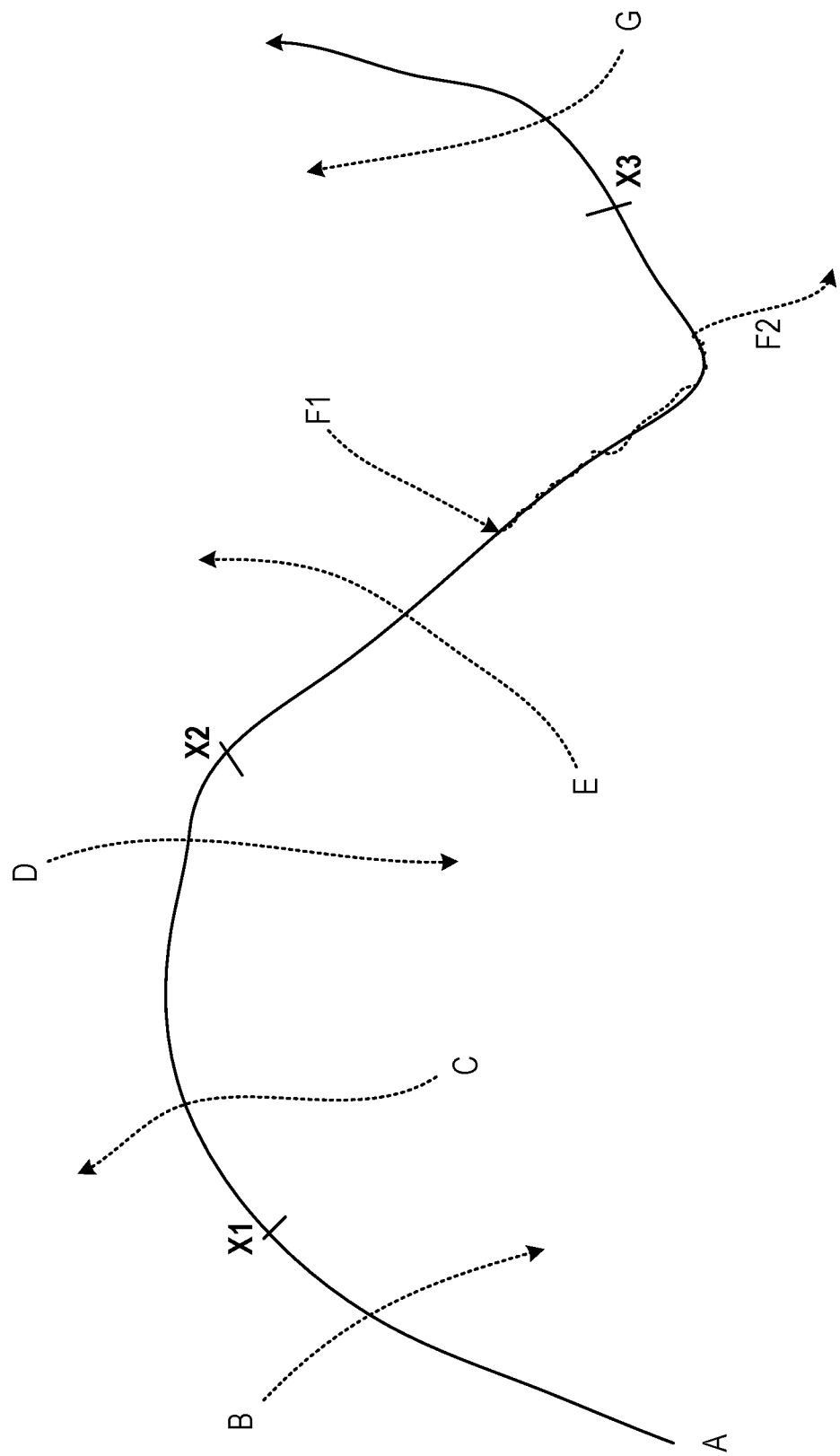
FIG. 9 depicts various examples of contact having occurred or contact possibly having occurred, between two or more persons.

FIG. 9 depicts various examples of contact having occurred or contact possibly having occurred, between two or more persons. The examples provide insights into at least some considerations that need to be made in selecting, generating, and comparing the geo-temporal patterns of the wireless terminals. The tracks of various people are shown and labeled as persons A through G, constructed from the geo-temporal data corresponding to each person's wireless terminal. Direction of tracks are shown by arrowheads. The tracks are determined from the geo-temporal data of the respective wireless terminals, and can be represented as mobility profiles generated at operation 403, which are then compared to one another at operation 405.

Illustratively, track A is that of an infected person ("person A"), whose wireless terminal's identifier (e.g., an IMSI, etc.) is made available for tracking purposes. Person A becomes infected with a pathogen of a particular disease at data point X1, reports first symptoms as having occurred around a date and time corresponding to data point X2. X1 can be derived from X2 based on the particular disease's incubation period. Person A is considered to be no longer contagious at a date and time corresponding to data point X3.

For purposes of clarity, the tracks of person A and the others are simplifications compared to what might be more typical tracks of people throughout a geographic area and during a prolonged interval of time. Accordingly, the positions of data points X1, X2, and X3 have been simplified compared to where they would be along an actual track of a person over many days of contagiousness. Similarly, the tracks of other persons in relation to person A have also been simplified.

Person B crosses paths (i.e., intersects) with person A's track. However, B is not at risk in regard to A because A is not considered to have been contagious at the time and place of intersection. Hence, a mobility profile—or another type of geo-temporal pattern, for that matter—corresponding to B need not be generated or considered.

Person C intersects person A's track, but was at the intersection point before person A was. Thus, person C is not at risk of infection from person A, even though A was already infected when A was at the intersection point. Hence, a mobility profile corresponding to C need not be generated or considered.

Person D intersects person A's track, and was at the intersection point after person A was. Thus, person D might be at risk of infection from person A. The level of risk depends on various factors described elsewhere herein, such as the lifespan/persistence of a pathogen of a predetermined disease, for example and without limitation. For example, surface stability is an important consideration, as D might touch a surface on which the pathogen is still present, which might constitute a first level of risk. Hence, these characteristics are relevant in defining and using a mobility profile corresponding to D, as already described.

Person E intersects person A's track, and was at the intersection point at the same time as A. In other words, A and E were proximate in space to each other. Thus, person E might be at risk of infection from person A. The level of risk depends on various factors described elsewhere herein, such as the lifespan/persistence of a pathogen of a predetermined disease and mode of transmission, for example and without limitation. For example, mode of transmission is an important consideration, as E might inhale the pathogen when A sneezes, which might constitute a second level of risk. Hence, these characteristics are relevant in defining and using a mobility profile corresponding to E, as already described.

Person F intersects person A's track, and A and F were proximate to each other, and for a sustained amount of time. Illustratively, F (as track F1) got on a bus that A was already on and got off the bus later (as track F2). Thus, person F might be at risk of infection from person A. The level of risk depends on various factors described elsewhere herein, such as the lifespan/persistence of a pathogen of a predetermined disease and mode of transmission and amount of time exposed to the infected person or area, for example and without limitation. For example, exposure time is an important consideration, as F has more opportunities for infection if A and F are proximate to each other for a prolonged amount of time, accordingly, this might constitute a third level of risk. Hence, these characteristics are relevant in defining and using a mobility profile corresponding to F, as already described.

Person G crosses paths (intersects) with person A's track. However, G is not at risk in regard to A because A is no longer considered to be contagious at the time and place of intersection. Hence, a mobility profile corresponding to G need not be generated or considered.

As those who are skilled in the art will appreciate after reading this specification, in some embodiments the various risk levels might be assigned according to a different set of situations than what is represented in FIG. 9.

Alternatively, the identities of one or more persons B through G might be known before the identity and track of person A. In such an alternative scenario, the purpose of an investigation might be to determine the identity of person A as an infecting person (e.g., an index case, etc.) responsible for having infected one or more other persons (e.g., one or more of persons B through G, etc.). In other words, a first person (candidate infecting person) can have infected both a second person (infected person) and a third person (infected person). In this case, the first person is still a candidate, but in terms of how that person (as an index case) might have infected the other two, instead of the first person possibly being infected by another.

For instance, persons E and F are confirmed to be infected with a pathogen. Persons E and F have not crossed each other's paths, so the identity of a third person needs to be determined. Various candidate geo-temporal patterns can be tried (e.g., those of A, B, C, D, and G) until it is determined that A's geo-temporal pattern has similarities that those of E and F. The candidate geo-temporal patterns that E's and F's geo-temporal patterns are compared against for similarity can be selected based on any of a number of attributes—for example, based on an extrapolation back in time to a range of times during which each of E and F might be gotten infected (e.g. all possible intersections last Tuesday for E and last Wednesday for F).

In particular, person E intersected with person A at the store, and person F intersected with person A at work—in this case, the exposure is direct person-to-person. Or it might be determined that person A touched a particular object (e.g., a doorknob) or had been at a particular place (e.g., a store) prior to both E and F—in this case, the exposure is location-based. The infected location might be stationary, as in store, or it might be moving, such as person A having been in a vehicle (e.g., a taxi) prior to both E and F, which can be determined from the geo-temporal pattern showing similar movement (e.g., vehicular motion), albeit at different times, along a similar route (e.g., a street).

Figure 10:
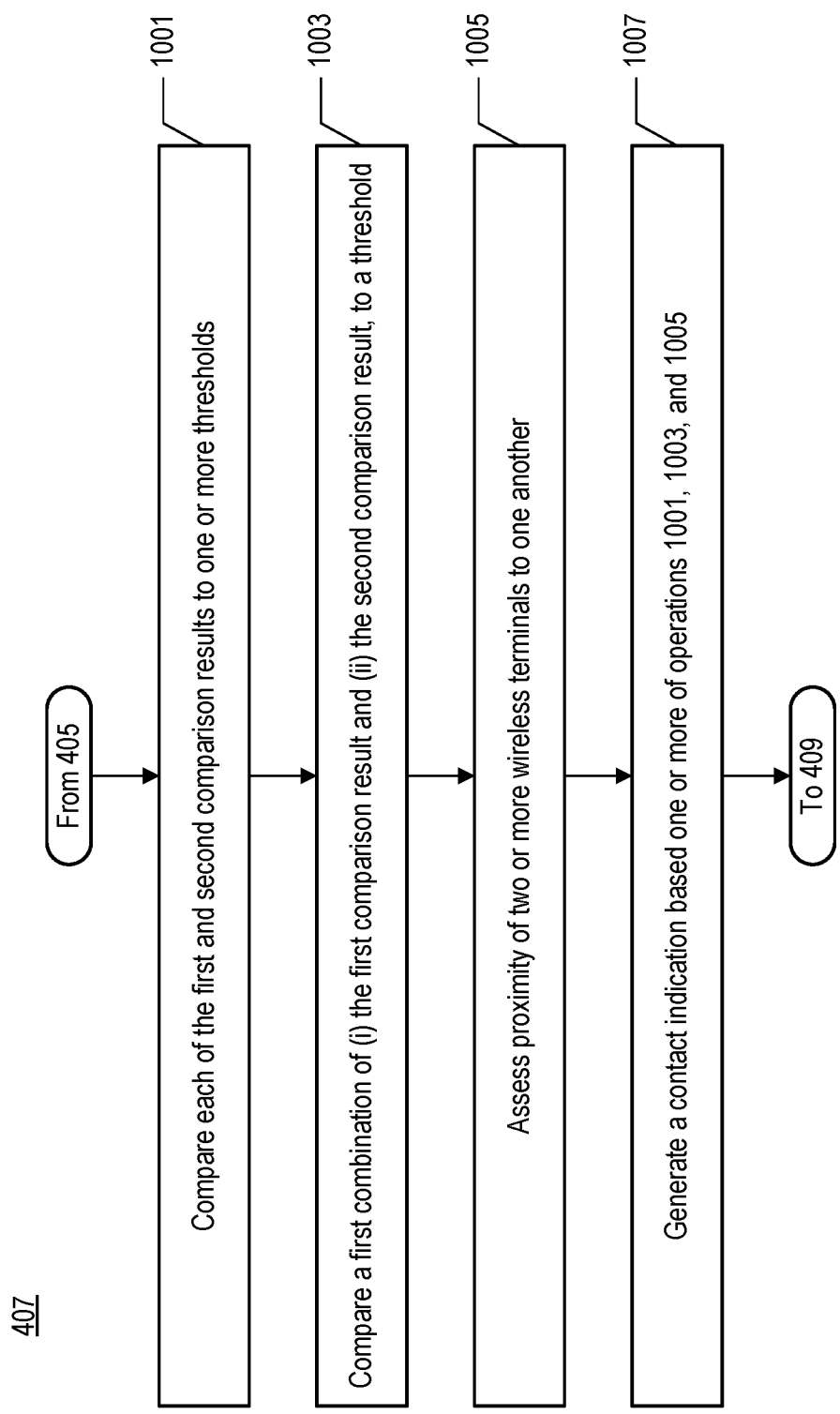
FIG. 10 depicts a flowchart of the salient sub-operations of operation 407.

FIG. 10 depicts a flowchart of the salient sub-operations of operation 407, in which geo-temporal analysis system 213 generates an indication of contact occurring between two or more persons.

At operation 1001, geo-temporal analysis system 213 compares each of the first and second comparison results to one or more thresholds. The specific values of the one or more thresholds can be determined through empirical analysis, for example and without limitation.

At operation 1003, geo-temporal analysis system 213 compares a first combination of (i) the first comparison result and (ii) the second comparison result, to a threshold. The specific value of the threshold can be determined through empirical analysis, for example and without limitation.

At operation 1005, geo-temporal analysis system 213 assesses proximity of two or more wireless terminals to one another based on radio signal data collected at operation 507 for electromagnetic signals transmitted directly between the wireless terminals. This results in an assessed proximity, wherein the assessed proximity is based on whether radio signals, as represented by the radio signal data, are transmitted between the wireless terminals of interest within at least one of the time periods in the plurality of time periods in the profile time interval of interest (e.g., the first profile time interval, etc.). The measures of closeness related to considering the electromagnetic signals that are described above and in regard to operation 405, can be additionally or alternatively applied here for the purpose of assessing proximity.

In some embodiments of the present invention, the assessed proximity is further based on whether the radio signals are transmitted between the wireless terminals of interest within at least N of the time periods in the applicable plurality of time periods making up the applicable profile time interval. The value of N can be based on one or more attributes. One or more of the attributes can be based on a first disease that a second user is diagnosed as having, for example and without limitation. Specific characteristics of the first disease (e.g., mode of transmission, etc.) on which the one or more attributes can be based are described elsewhere in this specification.

At operation 1007, geo-temporal analysis system 213 generates an indication of the inferred contact that occurred, if any, according to the outcomes of operations 1001 through 1005. Generally speaking, a parameter exceeding a threshold described in operation 1001 and 1003 can trigger generating of the indication of contact. An assessment of proximity at operation 1005 can also be probative of contact and can influence the indication of contact.

In some embodiments of the present invention, system 212 generates the indication of contact based on the first comparison result at operation 1001 exceeding a threshold that indicates a relative likelihood that the first user of wireless terminal 201 has come into contact with the second user of wireless terminal 202.

In some embodiments of the present invention, system 212 generates the indication of contact based on the second comparison result at operation 1001 exceeding a threshold that indicates a relative likelihood that the first user of wireless terminal 201 has come into contact with the third user of wireless terminal 203.

In some embodiments of the present invention, system 212 generates the indication of contact based on a first combination of (i) the first comparison result and (ii) the second comparison result exceeding a threshold that indicates a relative likelihood that the first user has come into contact with both (i) the second user and (ii) the third user.

In some embodiments of the present invention, system 212 generates the indication of contact is further based on whether both (i) at least one match is found to be present at operation 803 for all of the respective time periods between the first zone and the second zone and (ii) at least one match of zones visited by the first and third wireless terminals exists for a given time period.

After operation 1007, control of task execution proceeds to operation 409.

It is to be understood that the disclosure teaches just some examples according to illustrative embodiments of the present invention and that many variations of the present invention can be devised by those skilled in the art after reading this disclosure. The scope of the present invention is to be determined by the following claims.

What is claimed is:

1. A method for determining whether a first user of a first wireless terminal is an index case of a first disease, the method comprising:
    receiving location data for the first wireless terminal;
    generating a first mobility profile for the first wireless terminal, a second mobility profile for a second wireless terminal used by a second user, and a third mobility profile for a third wireless terminal used by a third user, wherein the generating of the first mobility profile comprises:
        (i) defining a first profile time interval that comprises a first plurality of time periods, the first profile time interval being defined by a first attribute, wherein the first attribute is based on a first disease that both the second user and the third user are diagnosed as having,
        (ii) aggregating, over the first profile time interval, selections of the location data for the first wireless terminal into corresponding zones in a second plurality of zones, and
        (iii) relating the zones in the second plurality to corresponding time periods in the first plurality;
    comparing the first mobility profile and the second mobility profile, resulting in a first comparison result;
    comparing the first mobility profile and the third mobility profile, resulting in a second comparison result; and
    generating an indication of contact based at least one of (i) the first comparison result and (ii) the second comparison result exceeding a first threshold that indicates a relative likelihood that the first user has come into contact with at least one of (i) the second user and (ii) the third user, respectively.

2. The method of claim 1, further comprising transmitting, based on the indication of contact being generated, at least one of:
    (i) the indication of contact, and
    (ii) a request for a location estimate of the first wireless terminal.

3. The method of claim 1, further comprising:
    receiving location data for the second wireless terminal;
    wherein the generating of the second mobility profile comprises:
        (i) defining a second profile time interval that comprises a third plurality of time periods, wherein the first profile time interval and the second profile time interval overlap with each other,
        (ii) aggregating, over the second profile time interval, selections of the location data for the second wireless terminal into corresponding zones in a fourth plurality of zones, and
        (iii) relating the zones in the fourth plurality to corresponding time periods in the third plurality.

4. The method of claim 3, wherein the comparing of the first mobility profile and the second mobility profile comprises:
    defining respective time periods between the first plurality of time periods and the third plurality of time periods; and
    for each of the respective time periods, comparing a first zone visited by the first wireless terminal in the second plurality of zones and a second zone visited by the second wireless terminal in the fourth plurality of zones;
    wherein a value of the first comparison result is based, at least in part, on the comparing of the first and second zones.

5. The method of claim 4, wherein a value of the first comparison result is further based, at least, at least in part, on how many matches of the first zone and the second zone are found to be present for all of the respective time periods.

6. The method of claim 4, wherein the indication of contact is further based on whether both (i) at least one match is found to be present for all of the respective time periods between the first zone and the second zone and (ii) at least one match of zones visited by the first and third wireless terminals exists for a given time period.

7. The method of claim 3, further comprising relating a first zone in the fourth plurality of zones to a corresponding first time period in the third plurality of time periods;
    wherein the first attribute is a first point in time that is based on when symptoms of the first disease appear for the second user, wherein the first time period comprises the first point in time, and wherein a value of the first comparison result is based, at least in part, on comparing (i) a first zone in the second plurality of zones for the first wireless terminal and (ii) a second zone in the fourth plurality of zones for the second wireless terminal.

8. The method of claim 7, wherein the first point in time is further based on when symptoms of the first disease appear for the third user.

9. The method of claim 1, wherein the indication of contact is further based on a first combination of (i) the first comparison result and (ii) the second comparison result exceeding a second threshold that indicates a relative likelihood that the first user has come into contact with both (i) the second user and (ii) the third user.

10. The method of claim 1, wherein the length of at least one of the time periods in the first plurality of time periods is based on a mode of transmission of the first disease.

11. A method for determining whether a first user of a first wireless terminal is an index case of a first disease, the method comprising:
    receiving location data for the first wireless terminal;
    generating a first mobility profile for the first wireless terminal, a second mobility profile for a second wireless terminal used by a second user, and a third mobility profile for a third wireless terminal used by a third user, wherein the generating of the first mobility profile comprises:
        (i) defining a first profile time interval that comprises a first plurality of time periods, the first profile time interval being defined by a first point in time and a second point in time, wherein the first point in time is based on when symptoms of a first disease appear for the second user, and wherein the second point in time is based on when symptoms of a first disease appear for the third user,
        (ii) aggregating, over the first profile time interval, selections of the location data for the first wireless terminal into corresponding zones in a second plurality of zones, and
        (iii) relating the zones in the second plurality to corresponding time periods in the first plurality;
    comparing the first mobility profile and the second mobility profile, resulting in a first comparison result;

comparing the first mobility profile and the third mobility profile, resulting in a second comparison result; and generating an indication of contact based on a first combination of (i) the first comparison result and (ii) the second comparison result exceeding a threshold that indicates a relative likelihood that the first user has come into contact with both (i) the second user and (ii) the third user.

12. The method of claim 11, further comprising transmitting, based on the indication of contact being generated, at least one of:
(i) the indication of contact, and
(ii) a request for a location estimate of the first wireless terminal.

13. The method of claim 11, further comprising:
receiving location data for the second wireless terminal;
wherein the generating of the second mobility profile comprises:
(i) defining a second profile time interval that comprises a third plurality of time periods, wherein the first profile time interval and the second profile time interval overlap with each other,
(ii) aggregating, over the second profile time interval, selections of the location data for the second wireless terminal into corresponding zones in a fourth plurality of zones, and
(iii) relating the zones in the fourth plurality to corresponding time periods in the third plurality.

14. The method of claim 13, wherein the comparing of the first mobility profile and the second mobility profile comprises:
defining respective time periods between the first plurality of time periods and the third plurality of time periods; and
for each of the respective time periods, comparing a first zone visited by the first wireless terminal in the second plurality of zones and a second zone visited by the second wireless terminal in the fourth plurality of zones;
wherein a value of the first comparison result is based, at least in part, on the comparing of the first and second zones.

15. The method of claim 14, wherein a value of the first comparison result is further based, at least, at least in part, on how many matches of the first zone and the second zone are found to be present for all of the respective time periods.

16. A method for determining whether a first user of a first wireless terminal is an index case of a first disease, the method comprising:
receiving location data for the first wireless terminal;
generating a first mobility profile for the first wireless terminal, a second mobility profile for a second wireless terminal used by a second user, and a third mobility profile for a third wireless terminal used by a third user, wherein the generating of the first mobility profile comprises:
(i) defining a first profile time interval that comprises a first plurality of time periods, the first profile time interval being defined by a first point in time and a second point in time, wherein the first point in time is based on when symptoms of a first disease appear for the second user, wherein the second point in time is based on when symptoms of a first disease appear for the third user, and wherein the length of at least one of the time periods in the first plurality of time periods is based on a mode of transmission of the first disease,
(ii) aggregating, over the first profile time interval, selections of the location data for the first wireless terminal into corresponding zones in a second plurality of zones, and
(iii) relating the zones in the second plurality to corresponding time periods in the first plurality;
comparing the first mobility profile and the second mobility profile, resulting in a first comparison result;
comparing the first mobility profile and the third mobility profile, resulting in a second comparison result; and
generating an indication of contact based at least one of (i) the first comparison result and (ii) the second comparison result exceeding a first threshold that indicates a relative likelihood that the first user has come into contact with at least one of (i) the second user and (ii) the third user, respectively.

17. The method of claim 16, further comprising transmitting, based on the indication of contact being generated, at least one of:
(i) the indication of contact, and
(ii) a request for a location estimate of the first wireless terminal.

18. The method of claim 16, further comprising:
receiving location data for the second wireless terminal;
wherein the generating of the second mobility profile comprises:
(i) defining a second profile time interval that comprises a third plurality of time periods, wherein the first profile time interval and the second profile time interval overlap with each other,
(ii) aggregating, over the second profile time interval, selections of the location data for the second wireless terminal into corresponding zones in a fourth plurality of zones, and
(iii) relating the zones in the fourth plurality to corresponding time periods in the third plurality.

19. The method of claim 18, wherein the comparing of the first mobility profile and the second mobility profile comprises:
defining respective time periods between the first plurality of time periods and the third plurality of time periods; and
for each of the respective time periods, comparing a first zone visited by the first wireless terminal in the second plurality of zones and a second zone visited by the second wireless terminal in the fourth plurality of zones;
wherein a value of the first comparison result is based, at least in part, on the comparing of the first and second zones.

20. The method of claim 19, wherein a value of the first comparison result is further based, at least, at least in part, on how many matches of the first zone and the second zone are found to be present for all of the respective time periods.

* * * * *